US011439429B2

(12) United States Patent
Zalewski et al.

(10) Patent No.: US 11,439,429 B2
(45) Date of Patent: Sep. 13, 2022

(54) CANNULA ASSEMBLY WITH DEPLOYABLE CAMERA

(71) Applicant: New View Surgical, Boston, MA (US)

(72) Inventors: Brandon M. Zalewski, Plymouth, CT (US); Arthur C. McKinley, Westport, MA (US); Jesse R. Plouffe, Willmington, MA (US); Bryce C. Klontz, Jr., Boston, MA (US); Jeffrey Karg, Bolton, MA (US); Paul DiCesare, Easton, CT (US); Danial P. Ferreira, Woodbridge, CT (US); Melvin B. Prenovitz, Newton, MA (US)

(73) Assignee: New View Surgical, Boston, MA (US)

( * ) Notice: Subject to any disclaimer, the term of this patent is extended or adjusted under 35 U.S.C. 154(b) by 341 days.

(21) Appl. No.: 16/508,738

(22) Filed: Jul. 11, 2019

(65) Prior Publication Data

US 2021/0007777 A1 Jan. 14, 2021

(51) Int. Cl.
*A61B 17/34* (2006.01)
*A61B 90/00* (2016.01)
(Continued)

(52) U.S. Cl.
CPC ............ *A61B 17/3423* (2013.01); *A61B 1/05* (2013.01); *A61B 1/0676* (2013.01);
(Continued)

(58) Field of Classification Search
CPC ..... A61B 17/34; A61B 17/3432; A61B 90/36; A61B 90/361; A61B 1/05; A61B 1/06; A61B 1/0676
See application file for complete search history.

(56) References Cited

U.S. PATENT DOCUMENTS 4,488,039 A 12/1984 Sato et al.
4,779,130 A 10/1988 Yabe
(Continued)

FOREIGN PATENT DOCUMENTS

EP 0556056 8/1993
WO WO 2008153841 12/2008

OTHER PUBLICATIONS

Cadeddu, J. et al., "Novel magnetically guided intra-abdominal camera to facilitate laparoendoscopic single-site surgery: initial human experience," Surg. Endoc. (2009) 23: 1894-1899.
(Continued)

*Primary Examiner* — Christopher J Beccia
(74) *Attorney, Agent, or Firm* — Farber LLC

(57) ABSTRACT

The present disclosure provides a cannula assembly having a tube with an internal lumen, a proximal end portion and a distal end portion configured for insertion into a patient. The cannula assembly further includes a housing rotatably coupled to the tube between a closed position and one or more open positions. The housing contains an electronic component comprising an image transmission device, such as a camera, for collecting and receiving images of the surgical site. The housing is adapted to provide the image transmission device with a longitudinal or forward view when the housing is in the closed position and a transverse view (i.e., offset from the longitudinal axis) when the housing is in one of the open positions. The housing is disposed distal to the proximal end portion and proximal to the distal end portion of the tube to protect the image transmission device as the distal end portion creates an incision and/or passes through an existing incision in the patient.

26 Claims, 18 Drawing Sheets

(51) Int. Cl.
*A61B 1/05* (2006.01)
*A61B 1/06* (2006.01)
*A61B 17/00* (2006.01)
*A61B 1/00* (2006.01)
*A61B 1/12* (2006.01)
*A61B 1/018* (2006.01)
*A61B 90/30* (2016.01)

(52) U.S. Cl.
CPC ........ *A61B 90/361* (2016.02); *A61B 1/00087* (2013.01); *A61B 1/00096* (2013.01); *A61B 1/018* (2013.01); *A61B 1/126* (2013.01); *A61B 17/00234* (2013.01); *A61B 17/3496* (2013.01); *A61B 90/30* (2016.02); *A61B 2017/3445* (2013.01)

(56) References Cited

U.S. PATENT DOCUMENTS

| | | | |
|---|---|---|---|
| 4,788,967 | A | 12/1988 | Ueda |
| 4,858,001 | A | 8/1989 | Milbank et al. |
| 5,166,787 | A | 11/1992 | Irion |
| 5,167,221 | A | 12/1992 | Chikama |
| 5,180,373 | A | 1/1993 | Green et al. |
| 5,183,471 | A | 2/1993 | Wilk |
| 5,256,149 | A | 10/1993 | Banik et al. |
| 5,305,121 | A | 4/1994 | Moll |
| 5,381,784 | A | 1/1995 | Adair |
| 5,443,484 | A | 8/1995 | Kirsch et al. |
| 5,448,990 | A | 9/1995 | De Faria-Correa |
| 5,506,912 | A | 4/1996 | Nagasaki et al. |
| 5,518,502 | A | 5/1996 | Kaplan et al. |
| 5,538,497 | A | 7/1996 | Hori |
| 5,569,160 | A | 10/1996 | Sauer et al. |
| 5,588,949 | A | 12/1996 | Taylor et al. |
| 5,603,702 | A | 2/1997 | Smith et al. |
| 5,630,795 | A | 5/1997 | Kuramoto et al. |
| 5,720,761 | A | 2/1998 | Kaali |
| 5,791,231 | A | 8/1998 | Cohn et al. |
| 5,797,943 | A | 8/1998 | Danks et al. |
| 5,860,996 | A | 1/1999 | Urban et al. |
| 5,891,013 | A | 4/1999 | Thompson |
| 5,899,851 | A | 5/1999 | Koninckx |
| 5,957,832 | A | 9/1999 | Taylor et al. |
| 6,097,423 | A | 8/2000 | Mattsson-Boze et al. |
| 6,348,034 | B1 | 2/2002 | Thompson |
| 6,371,909 | B1 | 4/2002 | Hoeg et al. |
| 6,387,043 | B1 | 5/2002 | Yoon |
| 6,478,730 | B1 | 11/2002 | Bala et al. |
| 6,478,806 | B2 | 11/2002 | McFarlane |
| 6,508,759 | B1 | 1/2003 | Taylor et al. |
| 6,527,704 | B1 | 3/2003 | Chang et al. |
| 6,648,817 | B2* | 11/2003 | Schara ............... H04N 13/254 348/E13.008 |
| 6,767,321 | B2 | 7/2004 | Czarnek et al. |
| 6,863,651 | B2 | 3/2005 | Remiian et al. |
| 6,916,286 | B2 | 7/2005 | Kazakevich |
| 6,984,203 | B2 | 1/2006 | Tartaglia et al. |
| 6,984,205 | B2* | 1/2006 | Gazdzinski .......... A61B 5/4255 600/407 |
| 6,986,738 | B2 | 1/2006 | Glukhovsky et al. |
| 7,037,258 | B2 | 5/2006 | Chatenever et al. |
| 7,041,052 | B2 | 5/2006 | Saadat et al. |
| 7,066,879 | B2 | 6/2006 | Fowler et al. |
| 7,322,934 | B2 | 1/2008 | Miyake |
| 7,585,273 | B2 | 9/2009 | Adler et al. |
| 7,604,648 | B2 | 10/2009 | Kerr |
| 7,758,603 | B2 | 7/2010 | Taylor et al. |
| 7,927,272 | B2 | 4/2011 | Bayer et al. |
| 7,967,744 | B2 | 6/2011 | Kaye et al. |
| 8,052,607 | B2 | 11/2011 | Byrd |
| 8,083,667 | B2 | 12/2011 | Cooper et al. |
| 8,105,233 | B2 | 1/2012 | Abou El Kheir et al. |
| 8,439,830 | B2 | 5/2013 | McKinley et al. |
| 8,834,358 | B2 | 9/2014 | Mckinley et al. |
| 8,940,009 | B2 | 1/2015 | Kahle et al. |
| 9,610,133 | B2 | 4/2017 | Ma et al. |
| 9,763,567 | B2 | 9/2017 | O'Prey et al. |
| 9,788,884 | B2 | 10/2017 | Viola |
| 2002/0049367 | A1 | 4/2002 | Irion et al. |
| 2003/0032863 | A1 | 2/2003 | Kazakevich |
| 2003/0055319 | A1 | 3/2003 | Chang |
| 2003/0236505 | A1 | 12/2003 | Bonadio et al. |
| 2005/0029978 | A1 | 2/2005 | Oleynikov et al. |
| 2005/0038317 | A1 | 2/2005 | Ratnakar |
| 2005/0059862 | A1 | 3/2005 | Phan |
| 2005/0085691 | A1 | 4/2005 | Nakao |
| 2005/0154256 | A1 | 7/2005 | Breidenthal et al. |
| 2005/0182293 | A1 | 8/2005 | Katzman |
| 2005/0234296 | A1 | 10/2005 | Saadat et al. |
| 2006/0006931 | A1 | 3/2006 | Farr |
| 2006/0106286 | A1 | 5/2006 | Wendlandt et al. |
| 2006/0183095 | A1 | 8/2006 | Komdorffer et al. |
| 2006/0252994 | A1 | 11/2006 | Ratnakar |
| 2007/0032701 | A1 | 2/2007 | Fowler et al. |
| 2007/0073109 | A1 | 3/2007 | Irion |
| 2007/0093812 | A1 | 4/2007 | Hayashida et al. |
| 2007/0179430 | A1 | 8/2007 | Smith et al. |
| 2007/0238931 | A1 | 10/2007 | Hanke |
| 2007/0249899 | A1 | 10/2007 | Seifert |
| 2008/0027279 | A1 | 1/2008 | Abou El Kheir et al. |
| 2008/0065099 | A1 | 3/2008 | Cooper et al. |
| 2008/0147018 | A1 | 6/2008 | Squilla et al. |
| 2008/0020800 | A1 | 8/2008 | Farr |
| 2008/0208006 | A1 | 10/2008 | Farr |
| 2008/0269557 | A1 | 10/2008 | Marescaux et al. |
| 2008/0269562 | A1 | 10/2008 | Marescaux et al. |
| 2009/0012530 | A1* | 1/2009 | Fowler .................. A61B 1/313 606/130 |
| 2009/0018400 | A1 | 1/2009 | Raymond et al. |
| 2009/0036744 | A1 | 2/2009 | Vayser |
| 2009/0259097 | A1 | 10/2009 | Thompson |
| 2009/0259102 | A1 | 10/2009 | Koninckx et al. |
| 2009/0275799 | A1 | 11/2009 | Saadat et al. |
| 2009/0312773 | A1 | 12/2009 | Cabrera et al. |
| 2010/0010504 | A1 | 1/2010 | Simaan et al. |
| 2010/0081875 | A1 | 4/2010 | Fowler et al. |
| 2010/0185197 | A1 | 7/2010 | Sakao et al. |
| 2010/0280316 | A1 | 11/2010 | Dietz et al. |
| 2011/0230894 | A1 | 9/2011 | Simaan et al. |
| 2012/0310044 | A1 | 12/2012 | Wendlandt et al. |
| 2014/0107417 | A1* | 4/2014 | McKinley ................ A61B 1/05 600/112 |
| 2017/0332887 | A1 | 11/2017 | Davis et al. |
| 2018/0256203 | A1 | 9/2018 | Rosenbaum et al. |

OTHER PUBLICATIONS

Fowler, D.L. et al., "Initial trial of a stereoscopic, insertable, remotely controlled camera for minimal access surgery," Surg. Endosc. (2010) 24:9-15.

International Search Report and Written Opinion for International Application No. PCT/US2010/028881 dated Oct. 29, 2010.

Karl Storz Full HD, "Optimized workflow," www.karlstorz-hd-endoscopy.com, (accessed Oct. 26, 2020).

\* cited by examiner

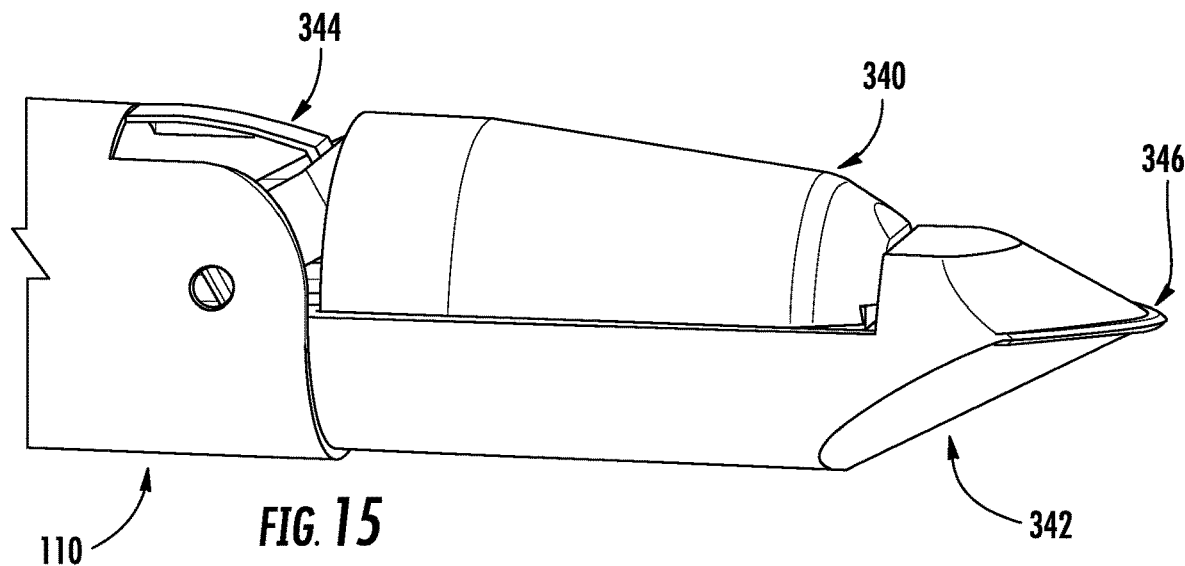
FIG. 15
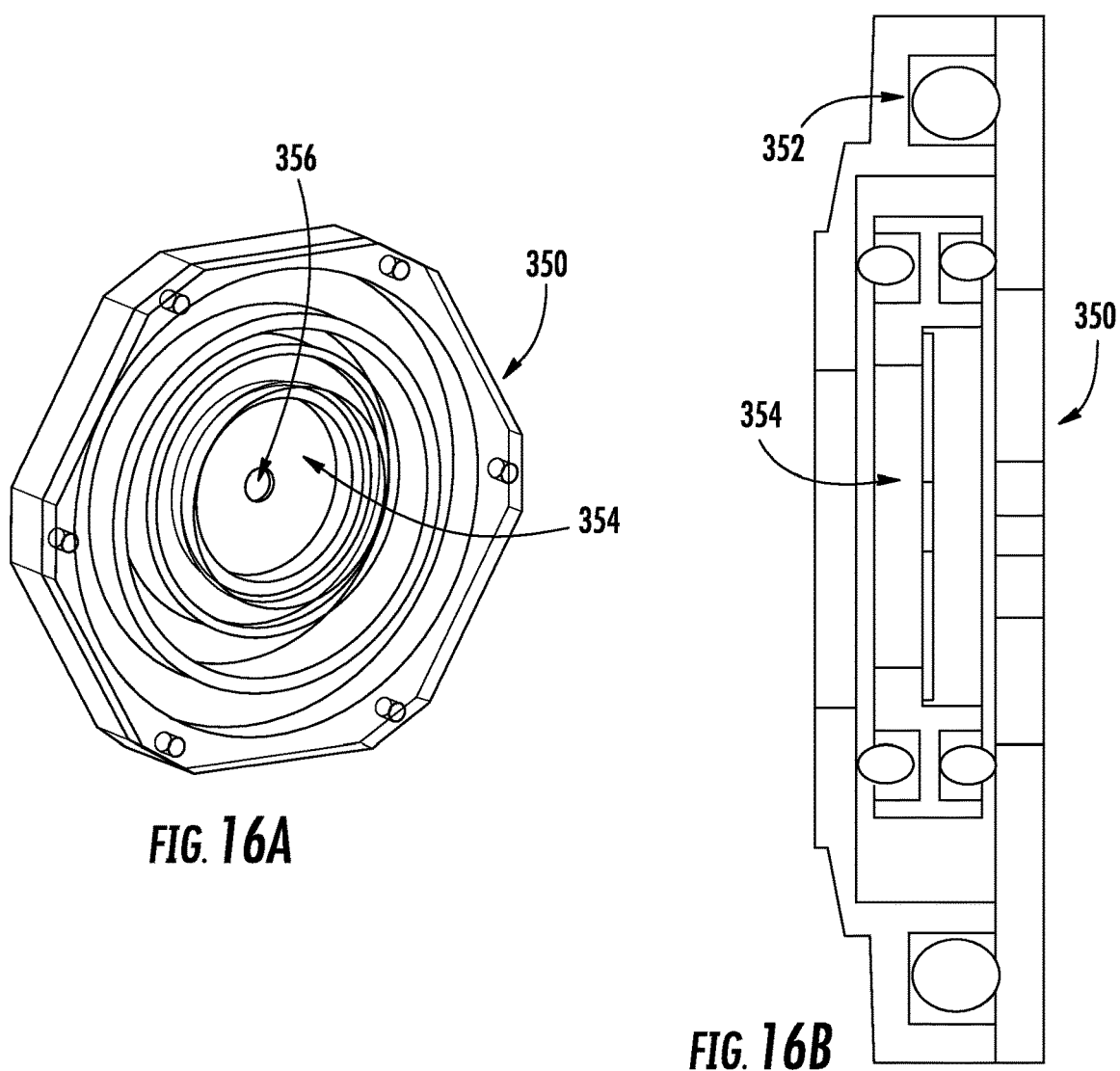
FIG. 16A
FIG. 16B

CANNULA ASSEMBLY WITH DEPLOYABLE CAMERA

BACKGROUND OF THE INVENTION

The field of the present disclosure relates generally to cannula assemblies with integrated imaging and illumination devices, and more particularly to cannulas with deployable cameras that provide a viewing angle offset from the cannula axis.

In minimally invasive surgery, there are often several small incisions made into the body to insert surgical tools, insufflation devices, endoscopes or other viewing devices. Endoscopic surgical procedures performed through a tubular cannula have evolved over the years. Presently, surgeons are performing endoscopic procedures in any hollow viscus of the torso body area after the region has been insufflated. Typically, multiple narrow cannulas are each inserted through individual small entrance wounds (i.e., ports) in the skin in order to accommodate various instruments, as well as different viewing angles. To accomplish their insertion, separate trocars are used in conjunction with the cannulas to puncture the body cavity. A trocar is a guide placed inside the cannula with either a pointed cutting blade, sharpened tip or a blunt tip, depending on whether it is used to puncture the skin or enter through a separately made incision. Once the cannula is inserted, the trocar is removed, leaving the hollow cannula in place for use during the procedure.

Surgeons are now doing procedures in a manner that minimizes the number of incisions to lessen trauma to the patient, reduce the incidence of infection, improve recovery time and decrease cosmetic damage. In certain cases, surgeons would prefer to only have one incision, referred to as Single Port Incision or Single Point Access (SPA). Surgeons are also using natural orifices, such as the mouth, to provide access for procedures using no incision or only incisions internal to the body.

The entry and deployment of imaging and/or lighting components can aid surgical procedures, such as endoscopic procedures. To minimize the number of access ports, cannulas with integrated imaging and lighting components have been developed. Examples of tubular cannula or catheters with deployable imaging and/or lighting components are described in U.S. Pat. No. 5,166,787 to Irion, U.S. Pat. No. 8,439,830 to McKinley, U.S. Pat. No. 8,052,607, US Patent Application No. 2009/0275799 to Sadat, US Patent Application No. 2009/0259097 to Thompson and US Patent Application No. 2008/0065099 to Cooper, and US Patent Nos. 2003/0032863 and 2007/0238931, the complete disclosures of which are hereby incorporated herein by reference in their entirety for all purposes.

Previous tubular cannula that incorporate integrated imaging and/or lighting components have certain drawbacks. In some cases, these devices comprise a camera mounted to the proximal end of the cannula, thereby limiting the view provided by the camera to the longitudinal axis of the cannula. In other cases, these devices include a deployable camera mounted to the distal end of the cannula. While this allows a broader view of the surgical area, it limits the design of the distal end of the cannula. Moreover, the optics of the imaging and lighting components can be damaged during movement of the device within the body cavity or during insertion and/or removal of the device. In particular, these designs expose the optics to potential damage when the distal end of the cannula is being used to create a percutaneous penetration or incision in the patient.

Accordingly, while the new systems and devices have proven highly effective and advantageous, still further improvements would be desirable. In general, it would be desirable to provide improved cannulas that incorporate integrated imaging and/or lighting components and are designed to protect the optics of these components during the procedure while having the ability to obtain one or more viewing angles that are offset from the cannula axis.

SUMMARY OF THE INVENTION

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides a cannula assembly having a tube with an internal lumen, a proximal end portion and a distal end portion configured for insertion into a patient. The cannula assembly further includes a housing rotatably coupled to the tube between a closed position and one or more open positions. The housing contains an electronic component comprising an image transmission device, such as a camera, for collecting and receiving images of the surgical site. The housing may further comprise illumination components, such as LEDs or the like, for illuminating the area around the surgical site. The housing is adapted to provide the image transmission and/or illumination devices with a longitudinal or forward view when the housing is in the closed position and a transverse view (i.e., offset from the longitudinal axis) when the housing is in one of the open positions. The housing is disposed distal to the proximal end portion and proximal to the distal end portion of the tube to protect the electronic components within the housing as the distal end portion creates an incision and/or passes through an existing incision in the patient.

The cannula assembly of the present invention combines the cannula, imaging and/or illumination functions into a single device to make it easier to control the access, imaging and instrument use during minimally invasive surgery while using fewer incisions in the patient. Positioning the housing distal of the proximal end portion of the tube provides the image transmission components with the ability to provide both a longitudinal or forward view as well as a transverse view that is offset from the cannula axis. At the same time, positioning the housing proximal to the distal end portion of the tube protect the optics and electronic components of the imaging and illumination components while the cannula is being used to pass through an incision and maneuver around the surgical site, such as a body cavity within the patient.

In certain embodiments, the distal end portion of the tube is configured to create and/or pass through a percutaneous penetration in the patient (e.g., an incision, opening, access port, cannula, natural orifice or the like). The distal end portion may form a pointed tip, a blunt tip, or it may have a conical outer surface that extends distally to either a blunt or sharpened tip. In some embodiments, the distal end portion is removably coupled to the tube and configured to translate longitudinally through the inner lumen. In these embodiments, the distal end portion may be, for example, a trocar or obturator specifically designed to create an incision or expand an existing incision in the patient. In other embodiments, the distal end portion of the tube is integrated with the tube into one component that may have a sharpened or blunt distal tip. In all of these embodiments, the housing is spaced proximally from the distal end portion to avoid any interference between the housing and the distal end portion and to protect the electronic components therein.

In a preferred embodiment, the cannula assembly comprises a hinge coupled to the tube and the housing and configured to pivot the housing relative to the tube between the open and closed positions. In one such embodiment, the hinge comprises a flexible element having a proximal end coupled to the outer surface of the tube and a distal end coupled to the housing. The flexible element is configured to bend away from the tube such that the housing is spaced from the tube and disposed at a transverse angle relative to the tube. In another embodiment, the hinge is disposed within the tube, exterior to the tube or on the circumference of the tube. The cannula assembly further comprises an actuation mechanism coupled to the hinge and configured to transition the housing between the open and closed positions. The actuation mechanism may be a push rod, link, cable or other suitable actuator that is coupled to a proximal end of the cannula assembly. The cannula assembly may further comprise a proximal user interface for controlling the actuator, such as a knob on the handle of cannula assembly. Alternatively, the actuation mechanism may be coupled to a robotic control system for remote actuation by the operator.

In an exemplary embodiment, the cannula assembly includes one or more reflective surfaces within the tube and/or the housing to reflect light from the image transmission and/or illumination devices through the distal end portion of the tube when the housing is in the closed position. This provides a forward view along the cannula axis during insertion, retraction and maneuvering of the device. The cannula assembly may further include one or more substantially opaque walls within the tube and/or housing positioned to inhibit backscatter of light from the image transmission or illumination components. The reflective surface(s) and opaque wall(s) may be fixed to the tube such that they remain in place during movement of the housing, or they may be coupled to the housing to pivot therewith.

In another embodiment, the image transmission device includes a camera and a lens. The cannula assembly further comprises a wiper assembly housed within the tube. The wiper assembly includes an actuator and a wiper element. The actuator is configured to move the wiper element relative to the lens to clean a surface of the lens. The wiper element may be a shuttle that slides through one or more channels formed in the housing, or it may comprise a wiper element coupled to a lateral arm that slides though one or more grooves in the housing. The actuator may comprise a spring, push rod, cable or other suitable actuating mechanism coupled to the wiper element and a user interface at the proximal end of the cannula assembly. In an exemplary embodiment, the wiper assembly further comprises a biasing element, such as a spring, that biases the wiper element in a position that does not interfere with the operation of the camera (i.e., spaced from the lens).

The device may further include an irrigation assembly having a fluid tube with a proximal end configured for coupling to a source of fluid and an open distal end adjacent to or near the wiper element. The irrigation assembly allows the operator to flush the camera lens with saline, surfactant or other fluid prior to actuating the wiper element. This provides a cleaner surface and makes the wiper assembly more effective.

In another aspect of the invention, a cannula assembly comprises a tube with an internal lumen, a proximal end portion and a distal end portion configured for insertion into a patient. The cannula assembly further includes a housing rotatably coupled to the tube between a closed position and one or more open positions. The housing contains an electronic component comprising an image transmission device, such as a camera, and/or illumination components for providing light to the surgical site. The housing is adapted to provide the image transmission and/or illumination device with a longitudinal or forward view when the housing is in the closed position and a transverse view (i.e., offset from the longitudinal axis) when the housing is in one of the open positions. The cannula assembly further comprises a projection extending into the interior of the housing and configured to engage the outer wall of the housing and/or the inner wall of the tube to inhibit movement of housing relative to the tube. This further protects the camera and light sources from damage during a surgical procedure.

In yet another aspect of the invention, a cannula assembly comprises a tube with an internal lumen, a proximal end portion and a distal end portion configured for insertion into a patient. The cannula assembly further includes a housing rotatably coupled to the tube between a closed position and one or more open positions. The housing contains an electronic component comprising an image transmission device, such as a camera, and/or illumination components. The housing is rotatable at least partially about a longitudinal axis of the tube such that the electronic component has at least a partial lateral view relative to this axis when the housing is in one of the open positions. The housing may be coupled to the tube via a hinge or other suitable pivot mechanism along one of its lateral sides such that the housing pivots at least partially (or completely) in the lateral direction relative to the cannula axis. This allows the operator to view either side of the tube or any combination of lateral/forward views during a surgical procedure. Alternatively, the housing may be rotatably coupled to the tube at the distal end of the housing (as opposed to the proximal end or lateral sides). In this configuration, the housing will rotate such that the image transmission and illumination components face in the proximal direction, providing the surgeon with a proximal view of the cannula (i.e., back to the incision).

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description serve to explain the principles of the disclosure.

FIG. 15 illustrates yet another embodiment of a cannula assembly according to the present invention;

FIGS. 16A and 16B illustrate one embodiment of a seal for the cannula assembly of the present invention;

DESCRIPTION OF THE EMBODIMENTS

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Figure 1:
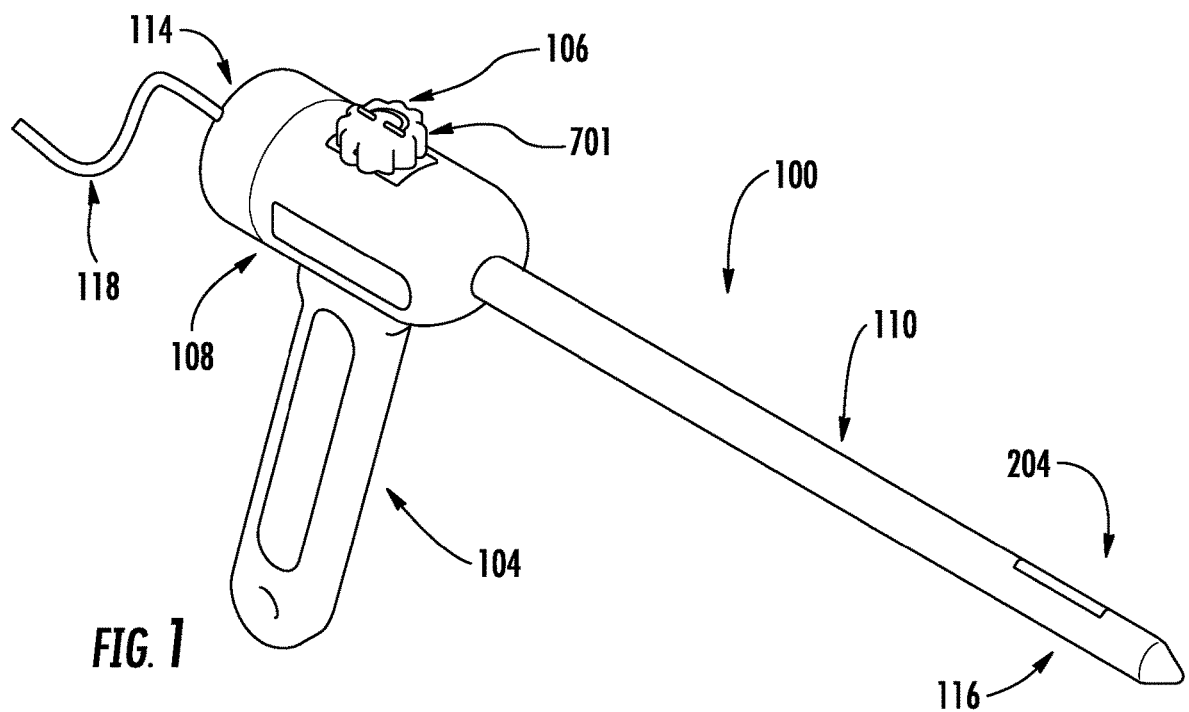
FIG. 1 depicts a schematic perspective view of a cannula assembly in a closed position, according to an embodiment of the present invention.
Figure 2:
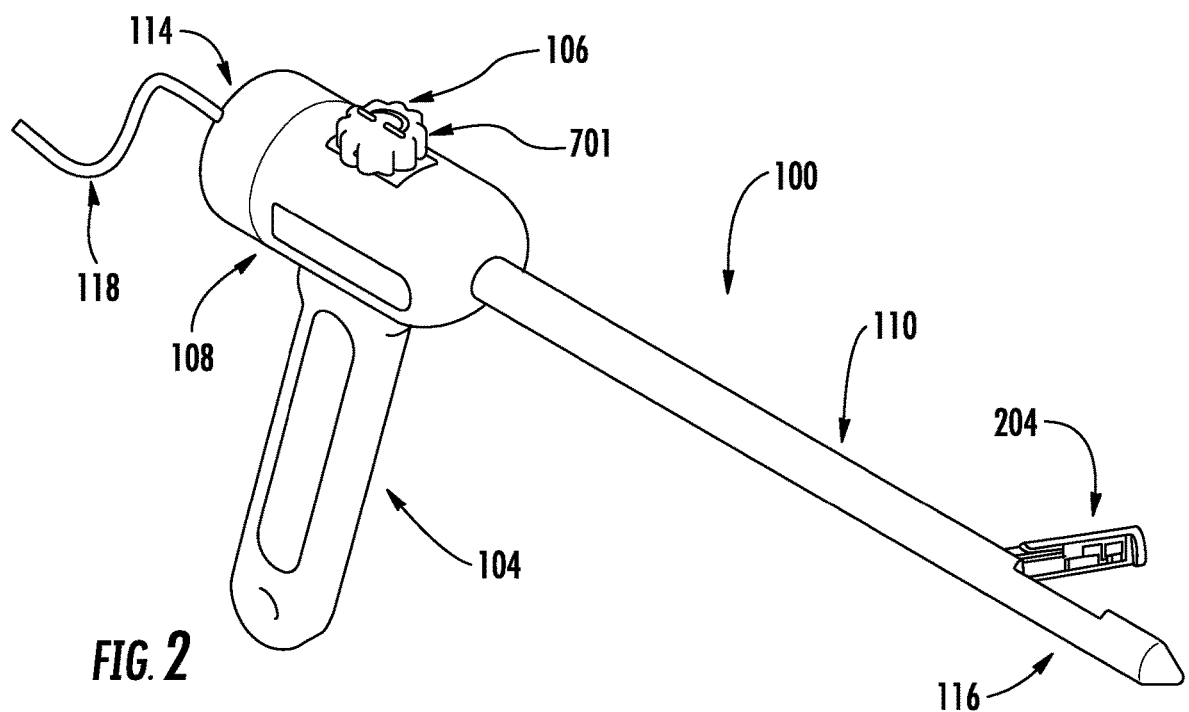
FIG. 2 depicts a schematic perspective view of the cannula assembly of FIG. 1 in one of its open positions.

FIGS. 1 and 2 illustrate one embodiment of a cannula assembly 100 in closed and open positions, respectively. Cannula assembly 100 includes a tube 110 forming an internal lumen 202 (see FIG. 3). A proximal end portion 114 of tube 110 can be adapted for manipulation by the surgeon or clinician, and a distal end portion 116 can be adapted for insertion through a percutaneous penetration and into a body cavity of a patient. In some embodiments, distal end 116 will be configured to create the percutaneous penetration and in other embodiments, distal end 116 will be configured to pass through an opening that has already been formed in the patient. For example, distal end 116 may be formed into a pointed tip, blunt tip or conical tip that is configured to puncture the patient's skin and pass through the incision created by the puncture. In other embodiments, lumen 202 of tube 110 can be fitted with a retractable and/or removable trocar (see, for example, distal end portion 116 in FIG. 3) for creation of the incision or percutaneous penetration. The blunt tip may include side sections or fins extending radially outward from the distal surface to facilitate access through an incision and/or to reduce the force necessary to create the incision. One example of a suitable blunt tip distal end for use with the present invention is an obturator described in U.S. Pat. No. 7,758,603, the complete disclosure of which is hereby incorporated by reference in its entirety for all purposes. Other suitable distal end portions for use in the present invention can be found in U.S. Pat. Nos. 8,940,009 and 6,478,806, the complete disclosures of which are hereby incorporated by reference in their entirety for all purposes.

Cannula assembly 100 further includes a housing 108 having a handle 104 attached near or at proximal end 114 of tube 110 for manipulation by the surgeon or the clinician. Tube 110 may be formed of a variety of cross-sectional shapes, e.g., generally round or cylindrical, ellipsoidal, triangular, square, rectangular, and D-shaped (in which one side is flat). One or more portions of tube 110 may be designed to open once inserted into the body cavity.

Figure 3:
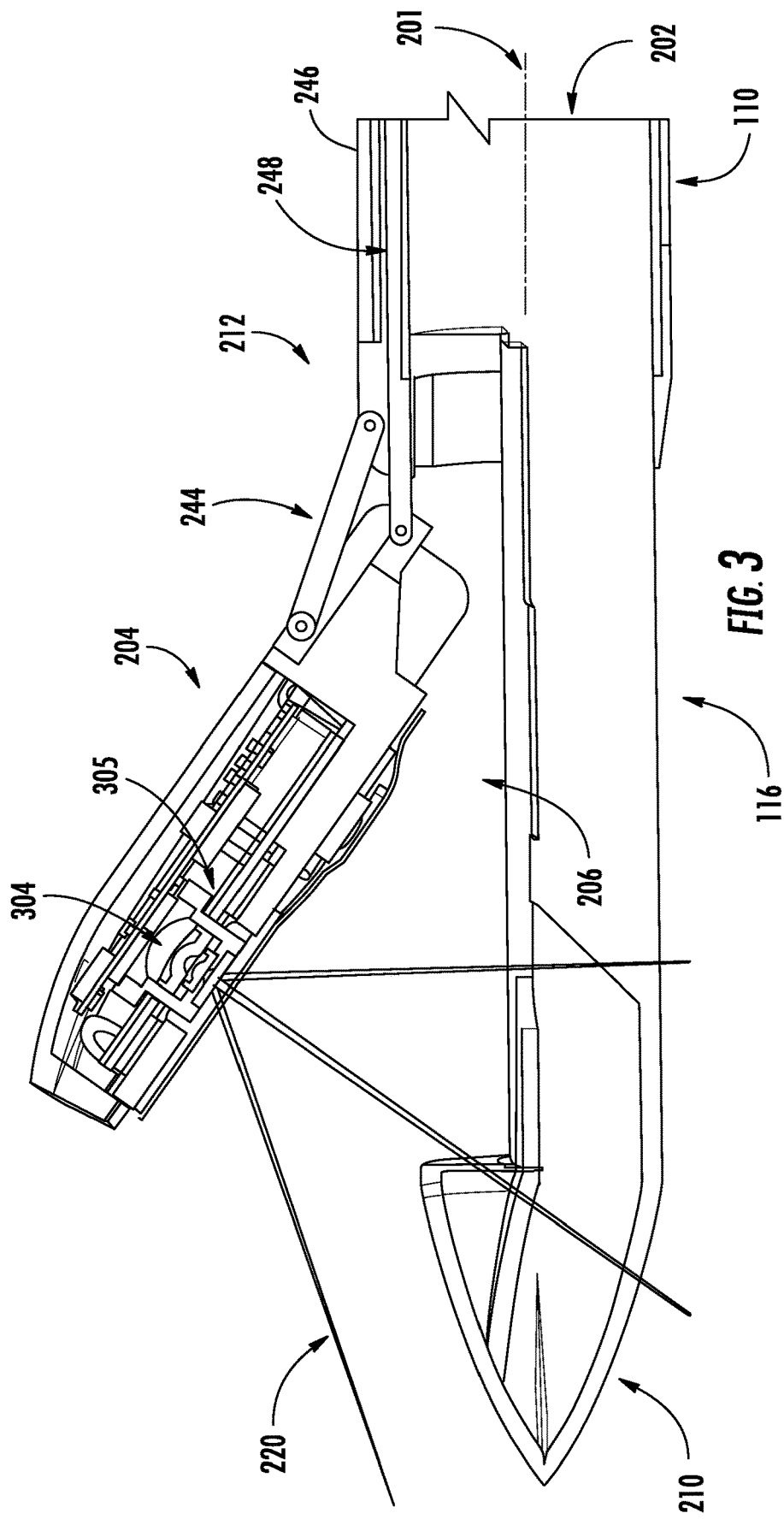
FIG. 3 is a side view of a distal portion of the cannula assembly illustrating an integrated camera/lighting assembly according to the present invention.

In one embodiment depicted in FIG. 3, cannula assembly 100 further includes a movable or deployable housing 204 coupled to tube 110 and designed to open and close relative to the remaining portions of tube 110. Housing 204 may be integral with tube 110 or it may be formed as a separate component that is coupled to tube 110. In either event, housing 204 is disposed on, or coupled to, tube 110 at a position proximal to distal end 116 and distal to proximal end 114. In the preferred embodiment, housing 204 resides far enough along tube 110 in the distal direction such that it is positioned within the body cavity of the patient during use. At the same time, housing 204 is positioned far enough proximal to distal end 116 such that it does not interfere with the insertion of distal end 116 of tube 110 as distal end 116 is passing the percutaneous penetration or incision in the patient. In addition, housing 204 is positioned proximally from distal end 116 to protect the electronic components therein (discussed below) as distal end 116 creates an incision and/or passes through an existing incision in the patient.

All or parts of cannula assembly 100 are capable of being positioned into the closed position for insertion and extraction either directly into the body cavity or through another insufflating cannula. In certain embodiments, tube 110 comprises an internal lumen 202 that can be fitted with a retractable and/or removable trocar. In one embodiment, the trocar is made of solid, non-transparent material. In another embodiment, all or parts of the trocar are made of optically transparent or transmissive material such that the trocar does not obstruct the view through the camera (discussed below).

Cannula assembly 100 further comprises an actuator mechanism that includes a proximal control 106 for moving housing 204 between the closed position (FIG. 1) and the open position (FIG. 2). Alternatively, proximal control 106 can incrementally move housing 204 between any number of positions between the open and closed positions. Proximal control 106 may be situated on handle 108 as shown in FIGS. 1 and 2, or it may be part of a robotic control system that is remotely controlled by an operator.

Housing 204 houses an electronic component, which is at least partially disposed within tube 110 when in the closed position. In certain embodiments, lumen 202 is substantially free from obstruction by the electronic components of housing 204 when in the closed position. This allows various instruments, e.g., surgical tools or other electronic components, to be passed through lumen 202 and used during the operation or surgical procedure. In other embodiments, the electronic components of housing 204 may partially obstruct lumen 202 in the closed position, but will not obstruct lumen 202 in the open position or at least some of the positions between the fully open and closed positions.

As shown in FIG. 3, the electronic components include one or more image transmission components 304, in combination with one or more illumination components 305. In one embodiment, image transmission component 304 may be a charge-coupled device (CCD) camera, a complementary metal oxide semi-conductor (CMOS) imaging device, and/or an imaging fiber optic cable and their ancillary optics and electronic drivers for power, communication and other functions. Optically, one or more of the image transmission components 304 may also image across the spectrum, including those portions invisible to the human eye, such as infrared and ultra-violet. In one embodiment, two image transmission components may be configured to capture stereoscopic images (in still and/or in motion). In one embodiment, one or more of the image transmission components 304 may be configured with any of a combination of fixed optics, adaptive optics, and/or active optics. Adaptive and active optics can be capable of focusing and/or zooming onto the image or target area.

In one embodiment, the one or more image transmission components 304 are capable of capturing both motion and still images, and transmitting them to the surgeon or operator through wired or wireless communication device 118 housed within or connected to the housing 108, handle 104, lumen 202 and/or the tubular element 110 wall. Such communication devices 118 may include electrical signals, such as analog and/or digital, or a fiber communication system.

The illumination component 305 may be one or more light or illumination sources and their ancillary electronic drivers. In one embodiment, the illumination sources are Light Emitting Diodes (LED), organic LED (OLED), illumination fiber optic, filament lamps, electroluminescent and/or laser sources. In certain embodiments, the illumination component 305 is tailored to work closely in both optical and spectrum characteristics with the image transmission component 304, with the illumination area, level and homogeneity being optimized. In one example, this may mean the illumination level is controlled by the surgeon or clinician; whereas, in another embodiment, Automated Gain Control (AGC) is correlated with the illumination level of the illumination component 305. A more complete description of suitable illumination and image transmission components can be found in U.S. Pat. No. 8,439,830 to McKinley, the complete disclosure of which is hereby incorporated by reference in its entirety for all purposes.

Figure 4:
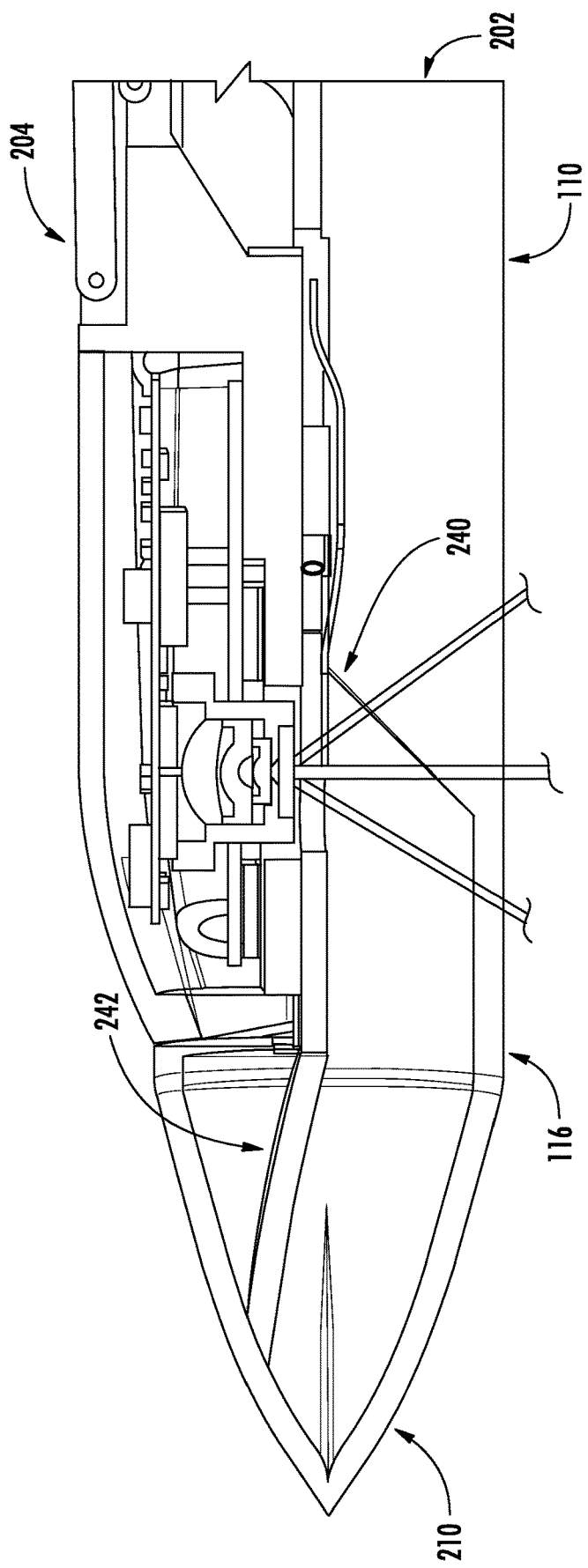
FIG. 4 is a side view of the cannula assembly of FIG. 3 illustrating a mirror/light path according to the present invention.

Referring now to FIGS. 3 and 4, a preferred embodiment of cannula assembly 100 will now be described (note that these figures only show the distal portion of cannula assembly 100). In this embodiment, distal end portion 116 is a separate component, such as a trocar, obturator or the like, that is removably coupled to tube 110 such that the distal end portion 116 may be translated in the longitudinal direction relative to tube 110 through lumen 202. For example, prior to insertion, housing 204 is opened and distal end portion 210 is translated through inner lumen 202 until it passes distally of the end of tube 110. Housing 204 is then closed and the obturator 116 can be used to create an incision, enlarge an incision or pass through an incision or other opening in the patient (as shown in FIG. 4). After tube 110 and housing 204 have been inserted through the incision and into the patient, housing 204 may be opened and distal end 116 retracted through internal lumen 202 of tube 110. Removal of distal end or obturator 116 provides an open internal lumen 202 to allow for the passage of instruments, tissue or the like through tube 110 during the surgical procedure.

In this embodiment, distal end 116 of tube 110 has a substantially conical outer surface 208 that extends to a relatively sharpened distal tip 210. However, it will be understood that distal end 116 may comprise a variety of different shapes and sizes, such as a substantially cylindrical or rectangular surface or a blunt end. Housing 206 is coupled to a distal end of tube 110 and sized to fit between distal tip 210 and tube 110 when housing 206 is in the closed position and distal tip 210 has been translated distally of tube 110, as show in FIG. 3. Of course, it will be recognized that distal end portion or obturator 116 may be integral with tube 110. In this embodiment, movable housing 204 is preferably sized to fit within a compartment 206 of tube 110 proximal to distal end 116 when in the closed position.

Housing 204 is preferably spaced away from distal tip 210 a sufficient distance to protect the electronic components therein as distal tip 210 is deployed to create and/or pass through an incision in the patient, or as tube 110 is maneuvered within a body cavity of the patient. In an exemplary embodiment, the proximal end of housing 204 is spaced at least about 5 mm to about 50 mm from the end of distal tip 210, preferably about 10 mm to about 40 mm, and more preferably about 20-30 mm.

Housing 204 is pivotally coupled to tube 110 via a hinge 212 that allows housing 204 to be pivoted away from tube 110 through a variety of different orientations between the closed and open positions. As shown, this provides the surgeon or operator with the ability to effectively "triangulate" one or more fields of views of the image transmission component and the illumination component. Adjusting the angle of the opening of deployable housing 204 relative to the longitudinal axis 201 of tube 110 causes the direction of view 220 to be adjusted without movement of the cannula. This allows the view to be changed slightly, without reverting to the need to move the cannula. In use, tube 110 may be rotated around axis 201 so that the image transmission and illumination components cover more fields of use. Alternatively, deployable housing 204 may be pivoted about more than one axis such that the direction of view can be lateral relative to axis 201 or even proximal along axis 201, as described below in reference to FIG. 11.

All or a portion of distal tip 210 of obturator 116 may be formed from an optically transparent material to allow the surgeon to see a forward view beyond distal end 116 (i.e., along axis 201 of tubular element 110). Tube 110 further includes an opening between housing 204 and inner lumen 202 of tube 110 to allow light from the image transmission and illumination sources to pass through. Cannula assembly 100 preferably includes one or more reflective surfaces 240, such as mirrors or the like, positioned at an angle relative to axis 201 such that the light emitted from image transmission components 304 and/or illumination components 305 reflects off surface(s) 240 and passes distally through distal tip 210. The reflective surface 240 may be coupled to a rod or other suitable connection (not shown) that passes through lumen 202 to proximal end 114, allowing surface 240 to be retracted from tube 110 once deployable housing 204 is opened, if necessary. Alternatively, reflective surface 240 may be part of the obturator 116, which is removed during operation.

Cannula assembly 100 further includes a substantially opaque surface or wall 242 extending from opening 238 to an internal surface of distal tip 210. Opaque wall 242 blocks light from the illumination elements 305 from passing directly into lumen 202 or distal end 116 (other than through opening 238) such that the light does not interfere with the image transmission components 304. This provides a much clearer view of the surgical field when the device is in the closed position and the surgeon is viewing forward along axis 201.

Referring again to FIG. 3, hinge 212 comprises a link 244 coupled to an upper surface of housing 204 and pivotally coupled to an outer surface 246 of tube 110 via pins or other suitable hinges. A push rod 248 is disposed within tube 110 and coupled to housing 204 and a proximal control knob 106 on handle 104 (see FIG. 1). Operation of knob 106 causes push rod 248 to translate distally or proximally. Distal translation of rod 248 forces housing 204 forward such that it pivots about link 244 into one or more open positions. In this configuration, imaging component 304 and illumination component 305 face the area of interest. The angle of opening of housing 204 may be adjusted by the amount of rod 248 fed into tube 110 by rotation of knob 106. This arrangement allows for the image and illumination components 304, 305 to occupy a portion of lumen 202 in the closed position, and to leave lumen 202 substantially open and available for instrument insertion, operation and/or removal when open. In addition, this arrangement protects the image and illumination components 304, 305 when closed.

Figure 5:
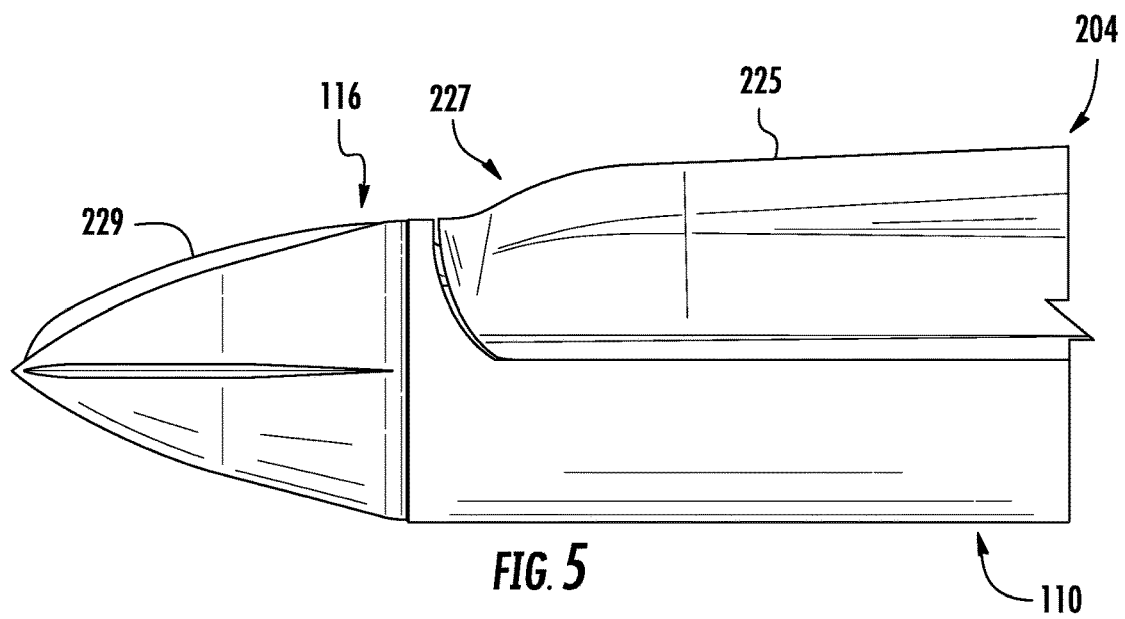
FIG. 5 is a side view of a distal end portion of the cannula assembly of FIG. 3 with a removable cover.

Referring now to FIG. 5, housing 204 may include a cover 225 over the outer surface of housing 204 to inhibit light from passing through housing 204 and inhibiting the operation of illumination and image transmission components. This improves the image quality of the view by the operator. To ensure that cover 225 remains secure during operation, housing 204 may further include an inclined distal surface or ramp 227. Distal end 116 may also include plurality of projections 229 extending radially outward from the conical surface to facilitate the passage of distal end 116 into or through an incision in the patient. Projections 229, for example, can be used to reduce the force required to push through the abdominal wall as distal tip 210 creates a passage therethrough.

Figure 6:
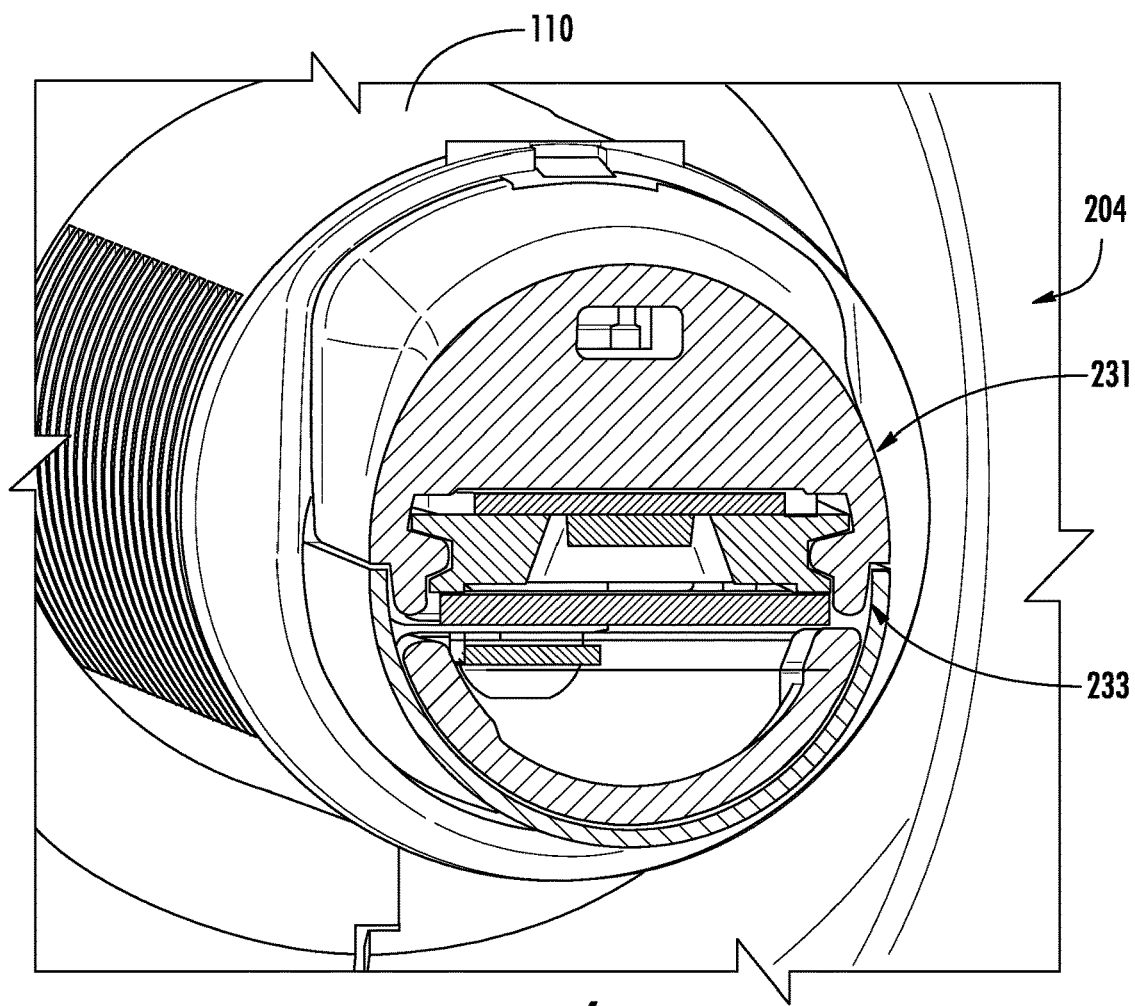
FIG. 6 is a cross-sectional view of the cannula assembly of FIG. 5.

FIG. 6 illustrates an internal cross-sectional view of housing 204 and tube 110. As shown, housing 204 includes an outer wall 231 extending around a hollow interior that houses the electronic components described above. In certain embodiments, outer wall 231 includes a projection or lip 233 extending into the hollow interior on either side of housing 204. Up 233 engages with tube 110 to inhibit side to side movement of housing 204 when tube 110 is being maneuvered in a surgical operation.

Figure 7:
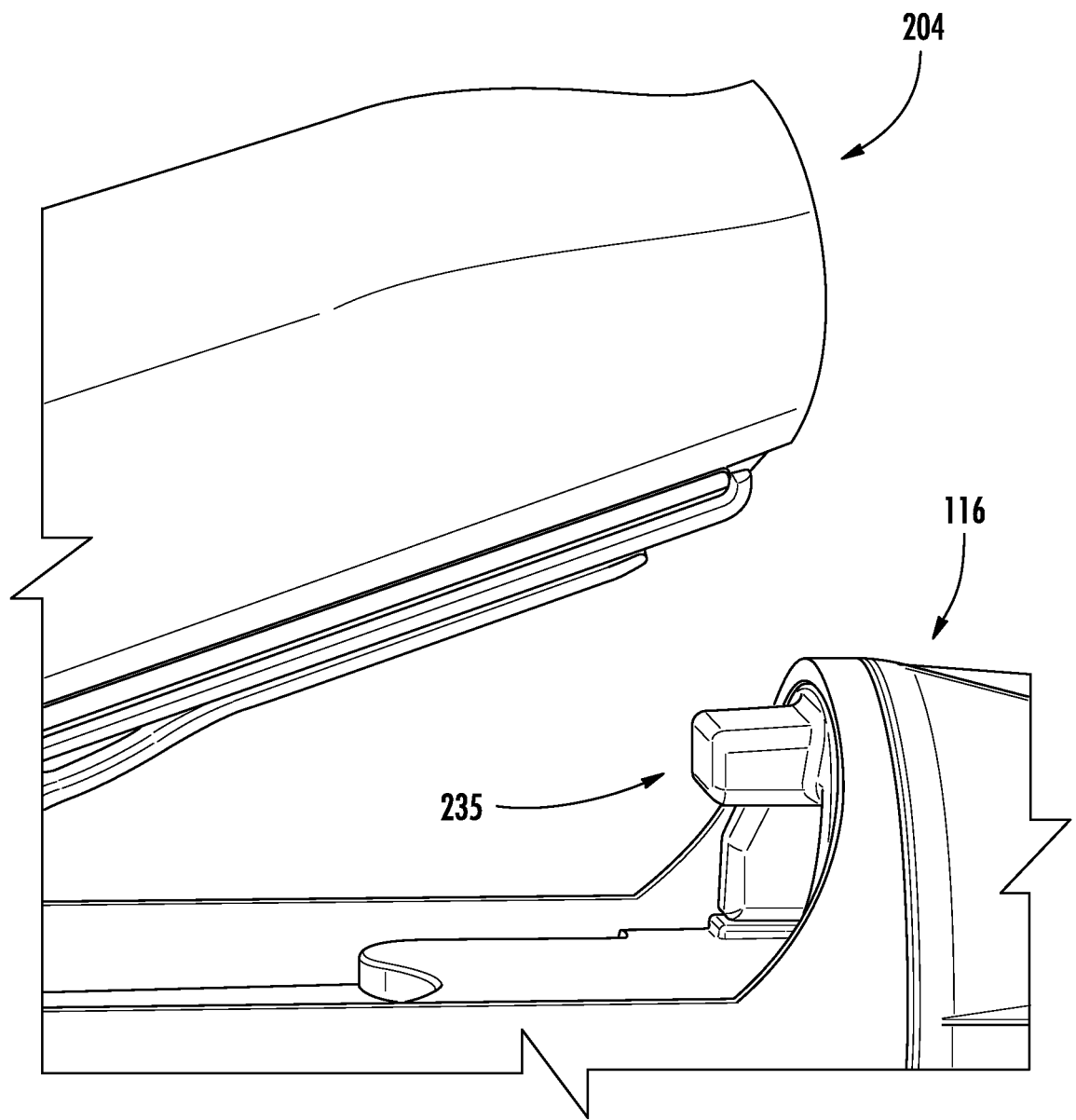
FIG. 7 is a side view of the camera/lighting assembly and a distal end portion of the cannula.

FIG. 7 illustrates an alternative embodiment wherein distal end portion 116 of cannula assembly 100 includes a projection or keying feature 235 extending into compartment 206 of tube 110. Keying feature 235 is sized to engage with an internal wall of housing 204 in the closed position to inhibit side to side movement of housing 204, thereby protecting the electronic components therein.

Figure 8A:
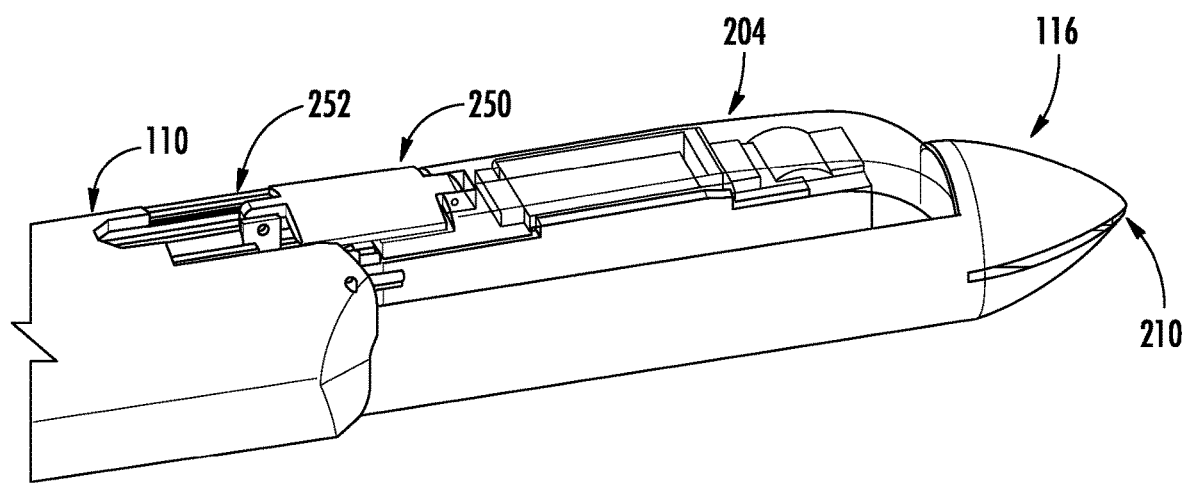
FIGS. 8A and 8B are perspective views of another embodiment of a distal portion of a cannula assembly with a hinge cover plate according to the present invention.
Figure 8B:
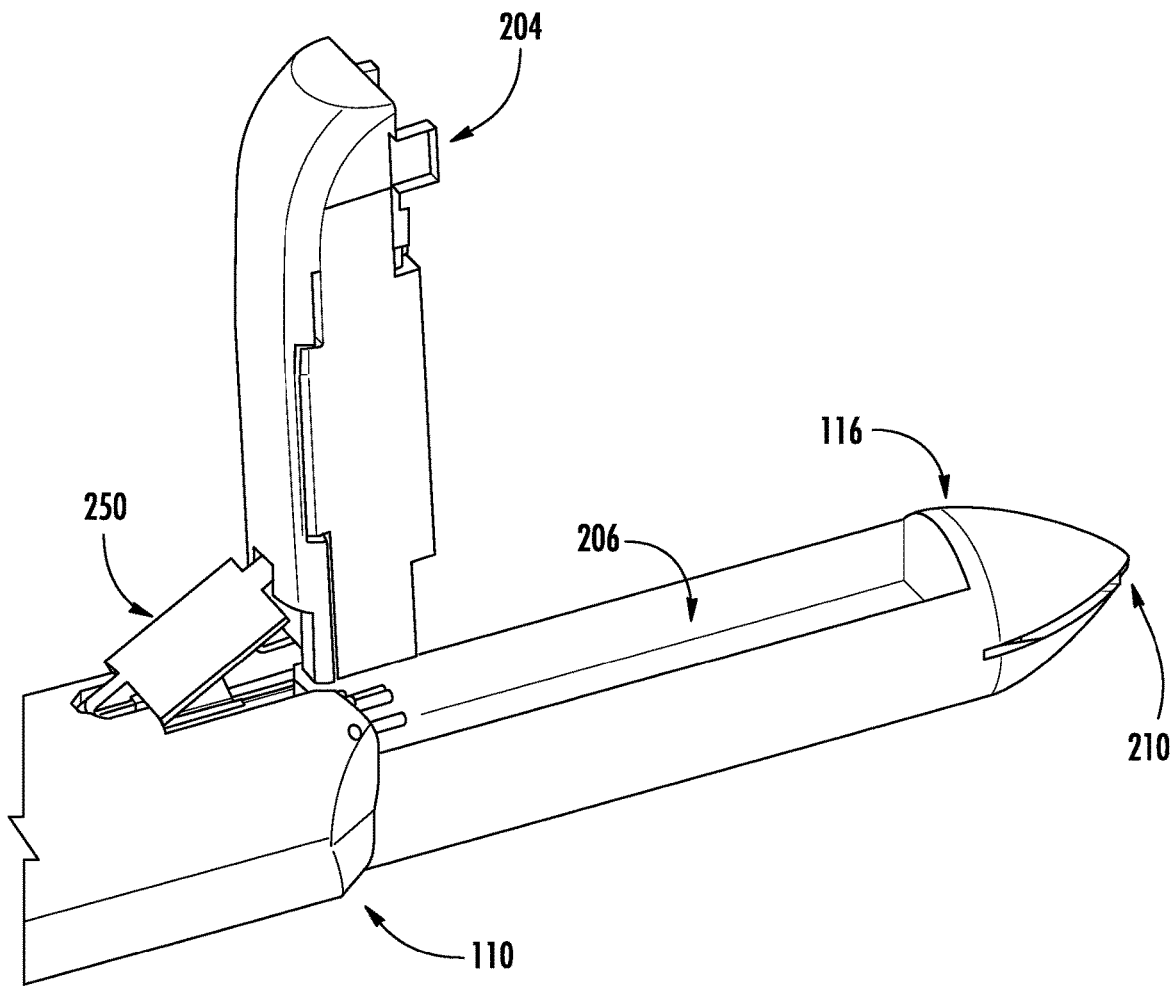

Referring now to FIGS. 8A and 8B, another embodiment of a cannula assembly 100 according to the present invention includes a deployable housing 204 dimensioned to fit within a compartment 206 of distal end portion or obturator 116. As in previous embodiments, housing 204 includes suitable image transmission and illumination components and is positioned proximal to distal tip 210 of the cannula assembly 100. In this embodiment, cannula assembly 100 includes a hinge cover plate 250 coupling deployable housing 204 with tube 110. Cover plate 250 is pivotally coupled to a linkage 252, which can be a push rod, cable, wire or other suitable actuator mechanism that extends through tube 110 to proximal end 114 of cannula assembly 100. As shown, proximal translation of linkage 252 pulls cover plate 250 proximally, thereby rotating d housing 204 away from tube 110 from a closed position (FIG. 5A) to an open position (FIG. 5B). As in previous embodiments, housing 204 may be rotated into any number of orientations between the open and closed positions.

Hinge cover plate 250 fits within a recess or opening in the upper surface of tube 110. Cover plate 250 is preferably sized to protect wires or other connection elements that extend between the image transmission and illumination components and proximal end 114 of cannula assembly 100.

Figure 9:
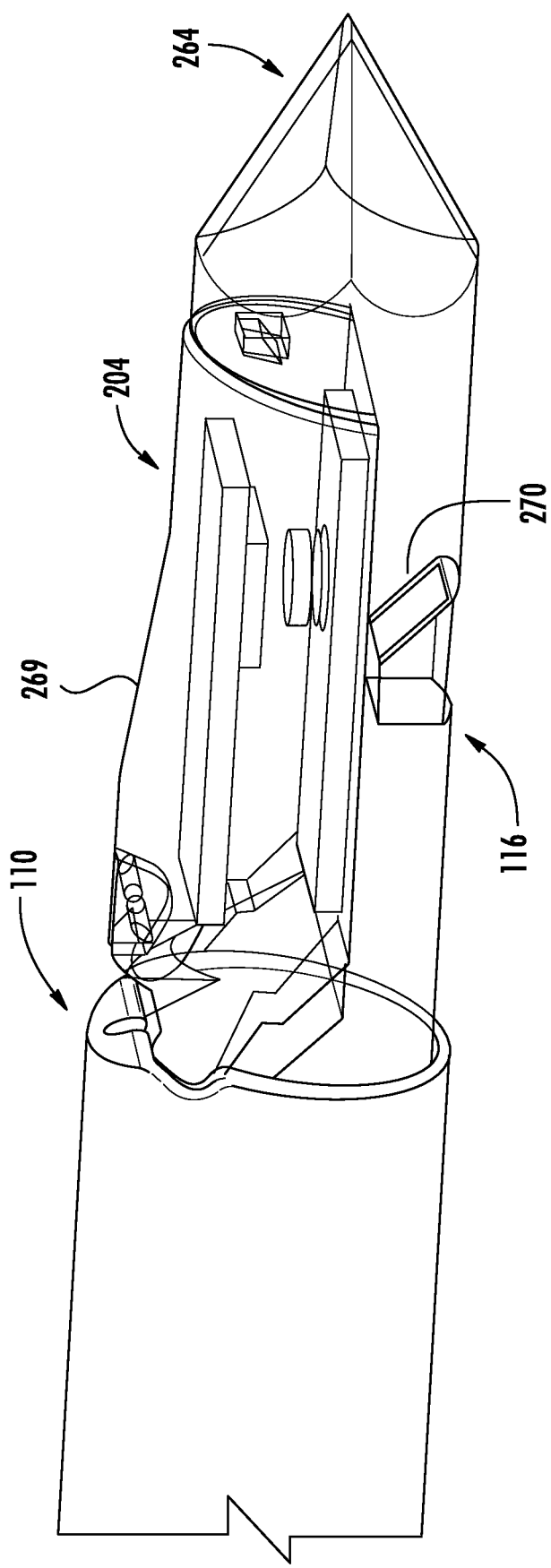
FIG. 9 is a perspective view of another embodiment of a cannula assembly with a cable hinge according to the present invention.

Referring now to FIG. 9, an alternative embodiment of cannula assembly 100 comprises a tube 110 removably coupled to a distal end portion 116. Distal end portion 116 comprises an obturator, trocar or other suitable device having a sharpened distal tip 264 for creating an incision or enlarging an existing incision in the patient A movable housing 204 rests within an open recess or compartment of distal end portion 116 such that the proximal end of housing 204 extends at least partially into tubular element 110 and the distal end of housing 204 is disposed proximally of sharpened cutting edge 264. In an exemplary embodiment, deployable housing 204 include a partially or fully transparent outer surface 269 surrounding the image transmission and illumination components housed therein. As in previous embodiments, distal end portion 116 includes one or more reflective surfaces 270 for reflecting light from image transmission and illumination components 304, 305 through cutting edge 264, thereby providing a forward view for the surgeon or operator.

In this embodiment, image transmission and illumination components 304, 305 may be designed to provide views offset from longitudinal axis 201 through transparent surface 269 in the closed position shown in FIG. 9. Thus, the camera may be facing upwards or laterally relative to longitudinal axis 201 so that it can provide views through transparent surface 269. Alternatively, housing 204 may be pivoted away from distal end portion 260 into one or more open positions to allow for such offset views (as described in the previous embodiments). To that end, cannula assembly 100 further includes one or more cables (not shown) that extend though tube 110 from the proximal end of housing 204 to proximal end 114 of tube 110. In an exemplary embodiment, the cables act as a thin flexible hinge, such as a living hinge, to pivot housing 204 between the open and closed positions.

Figure 10A:
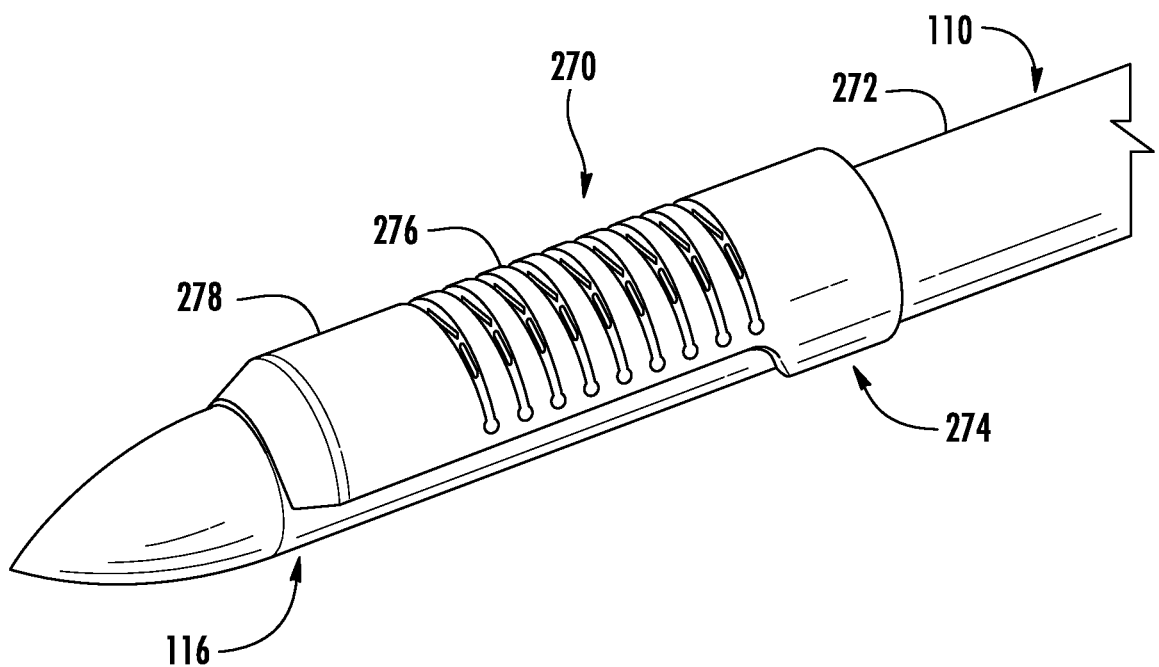
FIGS. 10A and 10B are perspective views of another embodiment of a cannula assembly with a flexible hinge according to the present invention.
Figure 10B:
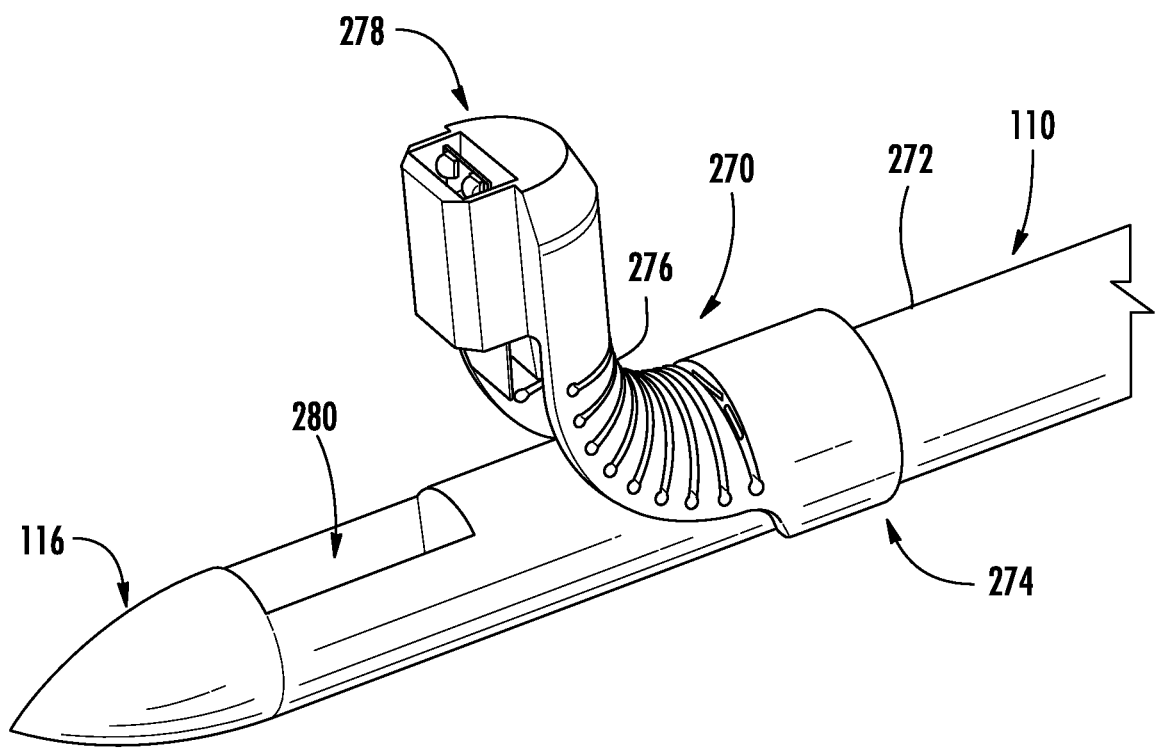

Referring now to FIGS. 10A and 10B, another embodiment of cannula assembly 100 includes a tube 110 and a flexible deployable element 270 coupled to an outer surface 272 of tube 110. In particular, flexible deployable element 270 comprises a substantially annular, proximal coupling element 274 sized to fit around outer surface 272 of tube 110 and couple element 270 to tube 110. Deployable element 270 further comprises a flexible component 276 extending from coupling element 274 to a distal housing 278. Housing 278 is sized to fit within a suitable compartment 280 within tube 110 or distal end portion 116 and to house the image transmission and illumination components. As in previous embodiments, housing 278 is disposed proximal of a distal end portion 116 to protect the image transmission and illumination components during use.

Flexible element 276 may comprise any suitable elastic or flexible material that allows element 276 to rotate or flex between a closed position (FIG. 7A) and an open position (FIG. 7B), thereby providing the image transmission and illumination components 304, 305 a view offset from axis 201. Flexible element 276 may be coupled to a suitable actuator mechanism (not shown) that allows the operator to rotate element 276 between the open and closed positions from handle 104 or a suitable robotic control system.

Figure 11:
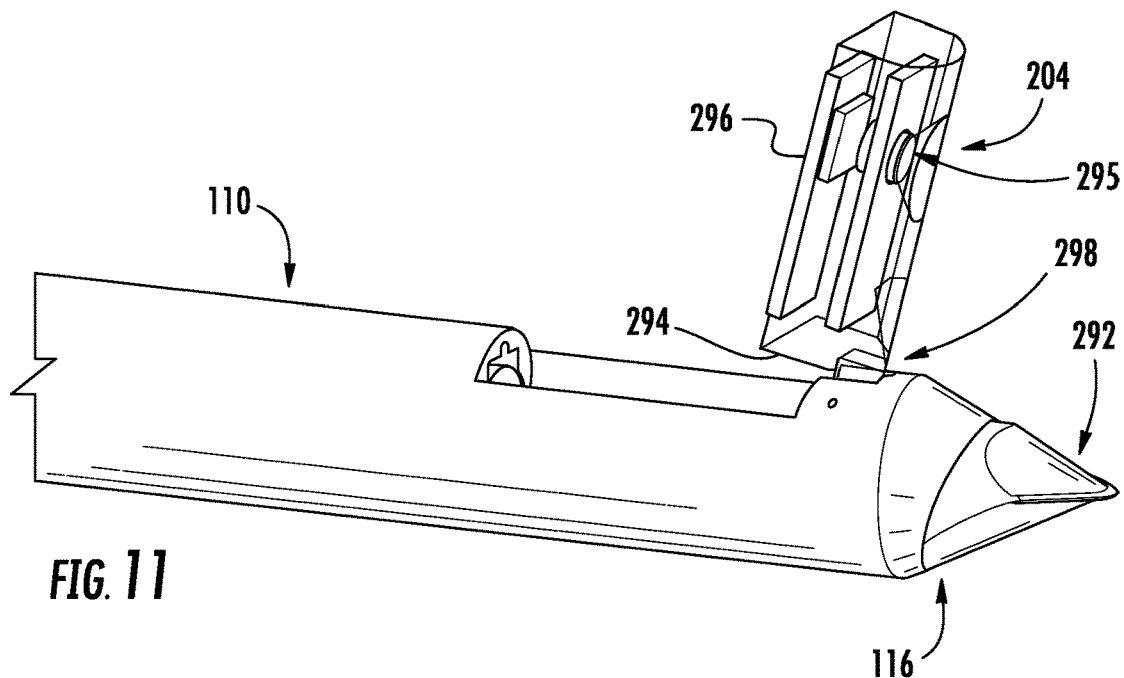
FIG. 11 is a perspective view of yet another embodiment of a cannula assembly with reverse and/or lateral views according to the present invention.

Referring now to FIG. 11, an alternative embodiment of cannula assembly 100 comprises a housing 204 containing suitable image transmission and illumination components 304, 305 and movably coupled to tube 110. As shown, deployable housing 204 is spaced proximally from a distal tip 292 of tube 110. In this embodiment, distal end portion 116 is integral with tube 110.

As shown, housing 204 is pivotally coupled to tube 110 at or near its distal end 294 such that housing 204 rotates laterally away from tube 110. In this configuration, camera 295 is rotated so that it still provides a forward or distal view in front of tube 110 in the open position. Providing a hinge at or near the distal end 294 of housing 204 reduces the chances that housing 204 may snag during insertion of the device into the patient. Alternatively, the hinge may be provided at one of the lateral sides 296 of housing 204. A second camera (not shown) may be included within housing 204 to provide a forward view when housing is in the closed position.

Alternatively, housing 204 may be capable of moving to a variety of different positions that are offset from the longitudinal axis 201 of tube 110. For example, housing 204 may be pivotally coupled to tube 110 at its distal end 294 such that housing 204 rotates away from tube 110 with the image transmission and illumination elements facing proximally back along tube 110 (i.e., towards the incision in the patient). In this embodiment, the surgeon or operator may choose to have a proximal view of the incision or the cannula.

Figure 11A:
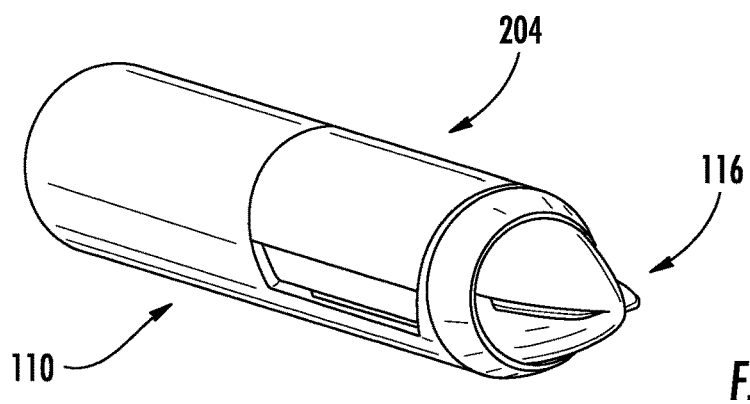
FIGS. 11A and 11B are perspective views of another embodiment of the cannula assembly with a lateral hinge according to the present invention.
Figure 11B:
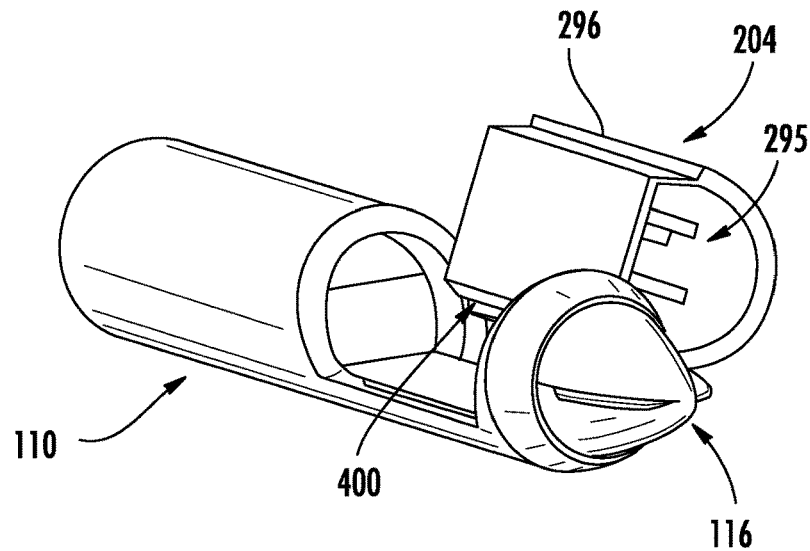

Alternatively, housing 204 may be pivotally coupled to tube 110 at one of its lateral sides 296 so that housing 204 pivots away from tube 110 laterally, thereby rendering a lateral view (i.e., towards either side of tube 110) (see FIGS. 11A and 11B). As shown, housing 204 comprises a hinge 400 on one side that allows housing 204 to rotate away from tube 110 in the lateral direction see FIG. 11B). In this embodiment, the camera 295 may face forward to provide a view along the side of tube 110, or it may face partially forward and partially upwards so that the camera 295 provides a view that is partially distal of tube 110 and partially above tube 110. In yet another embodiment, the camera 295 itself may be rotatable relative to housing 204 so that the operator can rotate the camera after housing 204 has pivoted to the side of tube 110. This moves the camera away from tube 110 such that rotation of camera 295 provides many different angles of view for the operator.

In another configuration, housing 204 may be coupled to tube 110 with multiple degrees of freedom such that housing 204 can be rotated in multiple directions relative to axis 201 (as shown in FIG. 11). For example, housing 204 may be pivotally coupled to tube 110 at one of its corners 298 with multiple hinges (not shown) such that housing can rotate with multiple degrees of freedom around, for example, an axis perpendicular to longitudinal axis 201, and an axis that is transverse to longitudinal axis 201. In this embodiment, the operator may have a partially lateral view of the surgical site (i.e., towards the sides of the cannula) as well as a partially forward (distal) or backward (proximal) view. As before, housing 204 may rotate from a fully closed position (i.e., 0 degrees relative to tube 110) to a fully open position (i.e., almost 180 degrees relative to tube 110). This allows the surgeon a full view above the cannula as well as on both sides of the cannula.

Figure 12A:
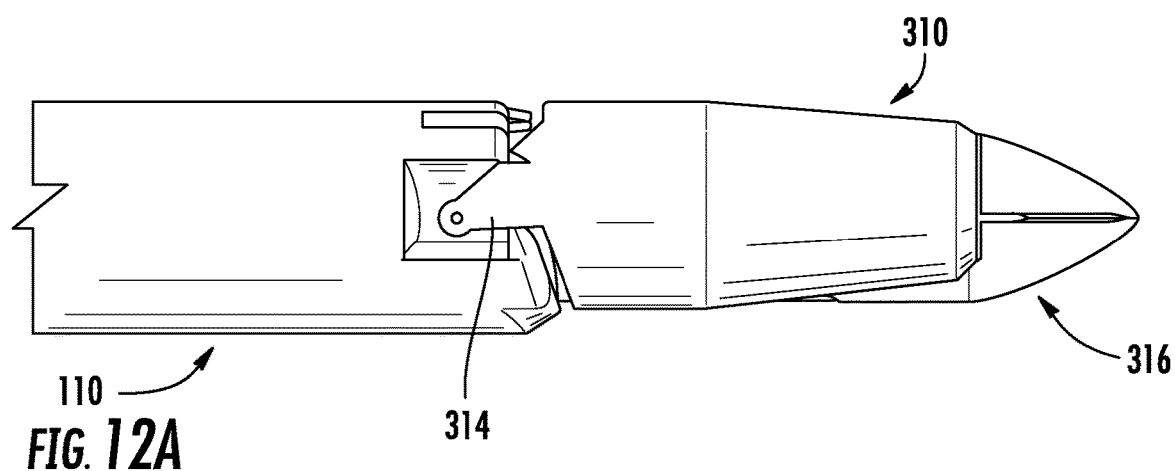
FIGS. 12A and 12B illustrate yet another embodiment of a cannula assembly with lateral hinges and a transparent distal end according to the present invention.
Figure 12B:
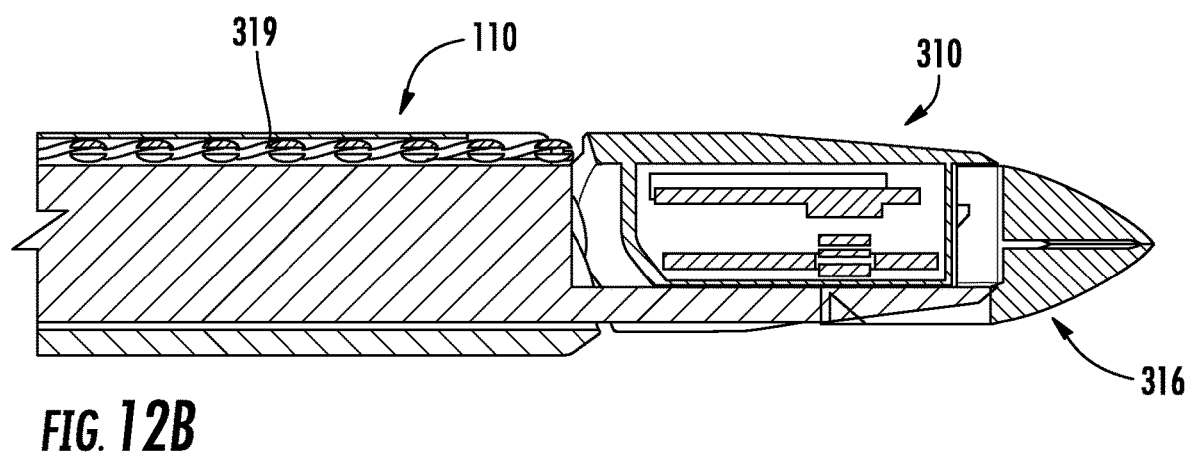

Referring now to FIGS. 12A and 12B, another embodiment of cannula assembly 100 includes a housing 310 either positioned within a compartment of tube 110 or positioned between the distal end of tube 110 and a removable distal end portion 316. In this embodiment, distal end portion 316 has a substantially conical shape configured to facilitate access through an incision in the patient. Housing 310 is spaced proximal to distal end portion 316 as in previous embodiments and is pivotally coupled to tube 110 with a pair of hinges 314 on either side of tube 110. Housing 310 is coupled to proximal end 114 of tube 110 via a suitable actuator mechanism, such as one or more cables 319 to open and close housing 310.

One of the advantages of this embodiment is that housing 316 has a substantially concentric shape relative to tube 110. This provides a more streamlined shape for passing cannula assembly 100 through an incision in the patient and/or maneuvering through a patient's body to the surgical site.

Figure 13:
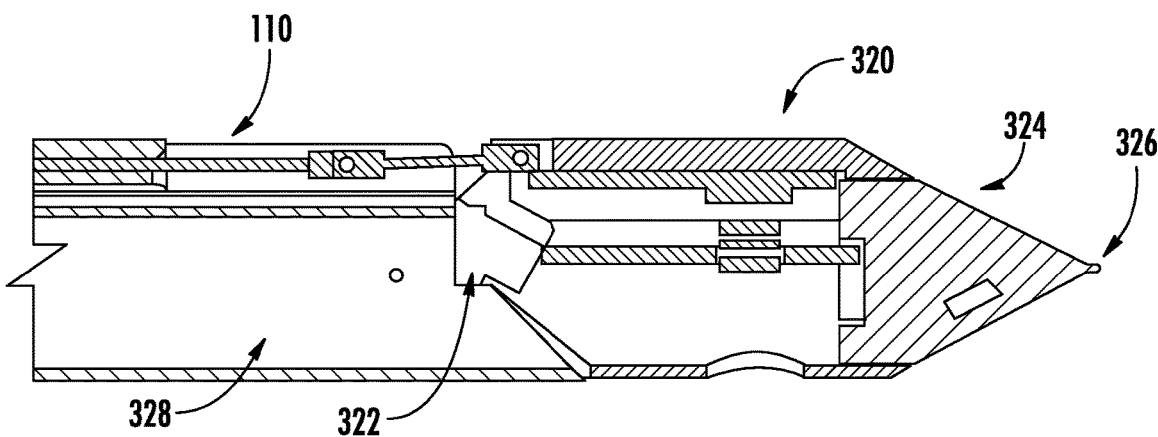
FIG. 13 illustrates another embodiment of a cannula assembly with lateral hinges and a solid distal end according to the present invention.

Referring now to FIG. 13, yet another embodiment of cannula assembly 100 includes a housing 320 coupled to tube 110 through a pair of hinges 322 similar to the previous embodiment. One or more linkages 323 couple housing 320 with the proximal end 114 of cannula assembly 100. In this configuration, housing 320 is formed integrally with a distal end portion 324, rather than as a separate component, such that both housing 320 and distal end portion 324 rotate into one or more open positions. Distal end portion 324 preferably comprises a relatively sharp cutting edge 326 to facilitate access through an incision in the patient. In the open positions, internal lumen 328 of tube 110 is open at the distal end of tube 110 such that instruments, trocars, tissue and the like can be passed therethrough unimpeded. As with previous embodiments, however, housing 320 is spaced proximally from distal tip 326 to protect the electronic components housed therein.

Figure 14:
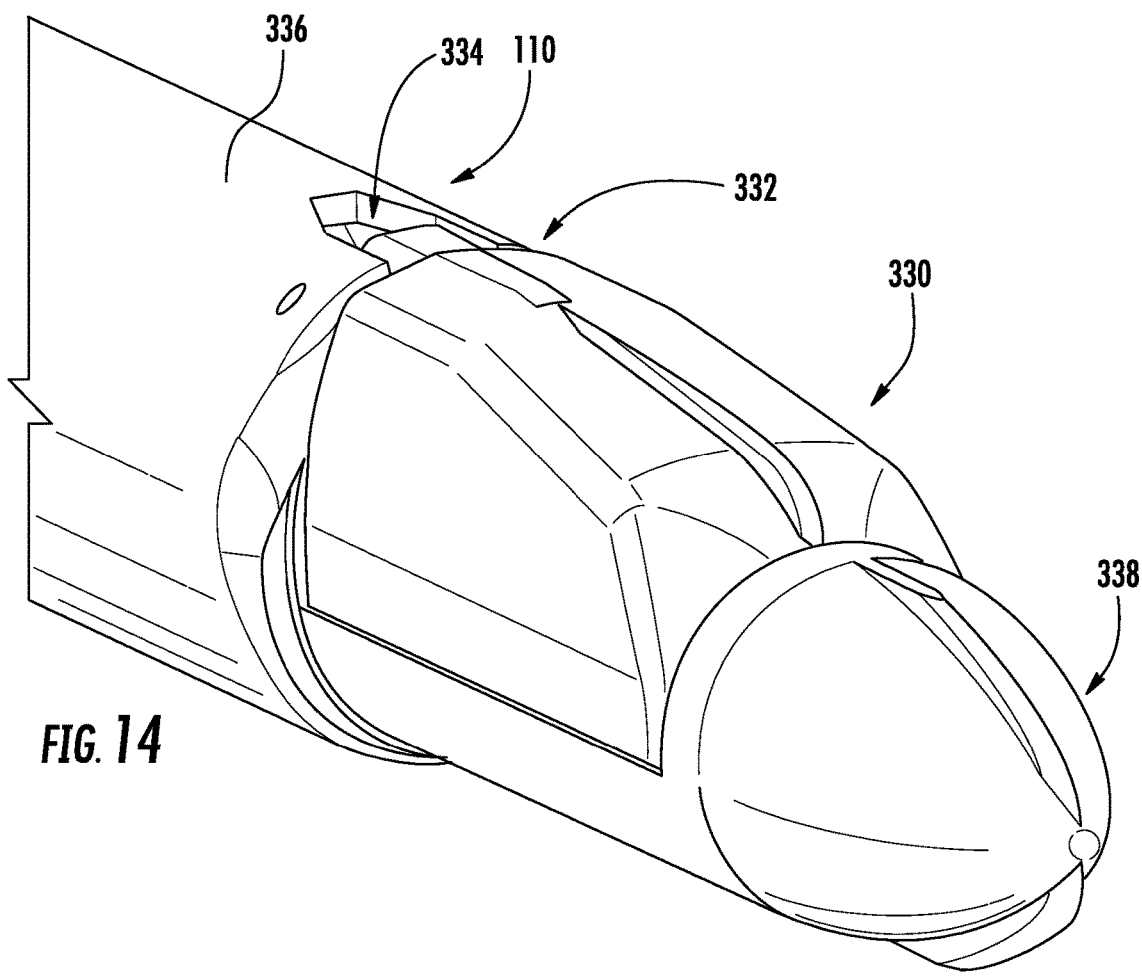
FIG. 14 illustrates another embodiment of a cannula assembly with a longitudinal hinge according to the present invention.

FIG. 14 illustrates yet another embodiment of cannula assembly 100 comprising a deployable housing 330 pivotally coupled to tube 110 at a hinge 332 mounted in a recess 334 in an upper surface 336 of tube 110. Of course, tube 110 may be rotated about axis 201 such that upper surface 336 is no longer positioned as the upper surface 336 during operation. Housing 330 is coupled to the proximal end 114 of cannula assembly 100 through a suitable actuation mechanism, such as a tube, rod, cable or the like. As in some of the previous embodiments, cannula assembly 100 comprises a distal end portion 338 that can be translated in the longitudinal direction relative to tube 110 and housing 330 when housing 330 is in one of the open positions. In the closed position shown, housing 330 is sized to fit between the distal end of tube 110 and distal end portion 338 when distal end portion 338 has been translated forward to a suitable location distal of tube 110.

FIG. 15 illustrates another embodiment of cannula assembly 100 comprising a housing 340 pivotally coupled to tube 110 and a distal end portion 342 configured for creating or passing through an incision in the patient. Distal end portion 342 preferably comprises a sharpened distal blade 346. Cannula assembly 100 includes a spring mechanism 344 configured to pivot housing 340 between the open and closed positions relative to tube 110 and distal end portion 342. In an exemplary embodiment, housing 340 comprises a sheet metal outer surface surrounding the interior image transmission and illumination components (not shown).

Referring now to FIGS. 16A and 16B, cannula assembly 100 may comprise a seal 350 for containing gases and fluids and maintaining a sterile enclosed surgical field. As shown, seal 350 comprises an outer annular ring 352 surrounding an internal flexible membrane 354. Ring 352 and membrane 354 comprise suitable flexible, elastomeric materials designed to maintain a tight fit around the inserted instrument during the surgical procedure. Membrane 354 comprises a small central opening 356 to facilitate the passage of such instruments. Of course, it will be understood that other seals may be used with the present invention to ensure that the entry-exit port of cannula assembly 100 remains closed, such as simple O-rings, quad rings, duckbill seals and the like.

Figure 17A:
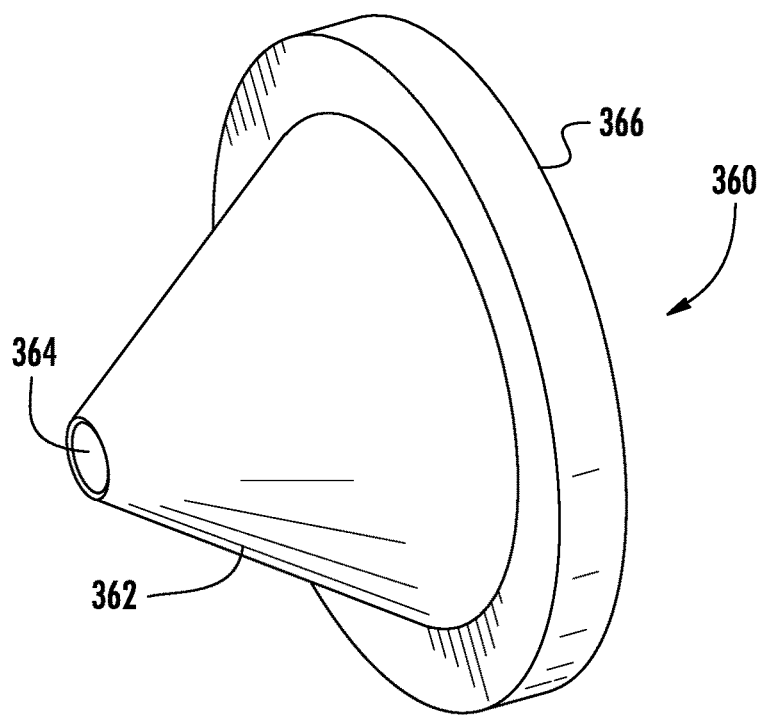
FIGS. 17A and 17b illustrate another embodiment of a seal for the cannula assembly of the present invention.
Figure 17B:
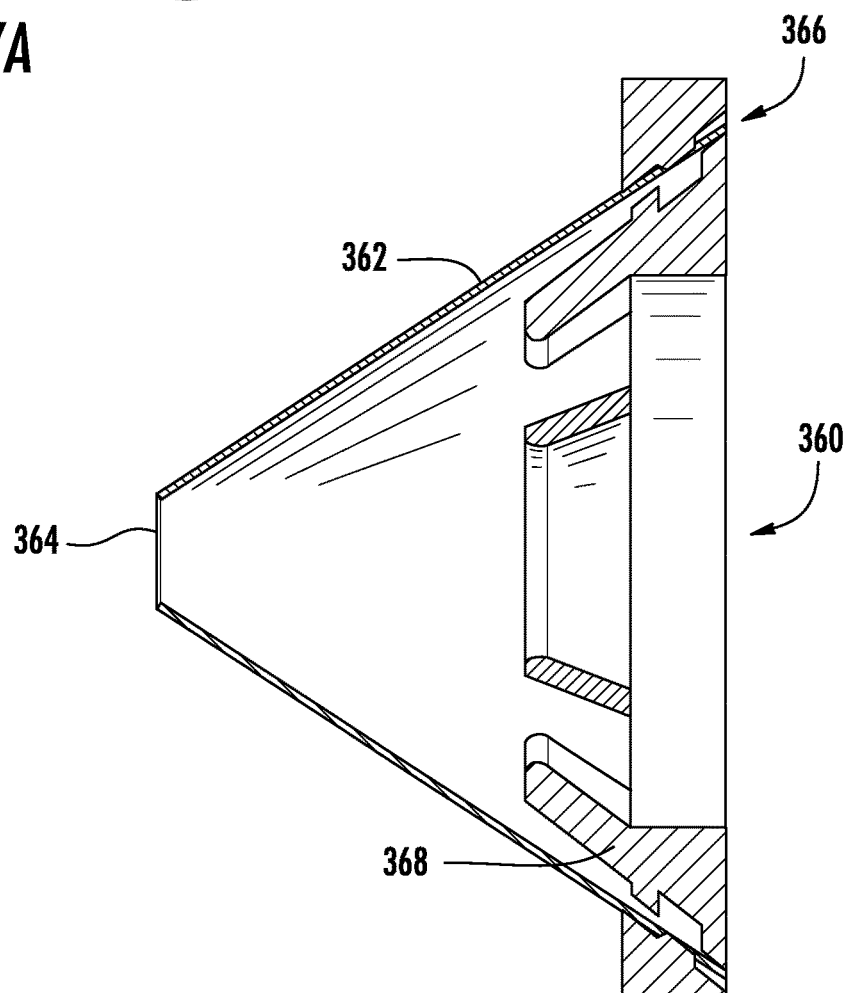

Referring now to FIGS. 17A and 17B, an alternative embodiment of a seal 360 for use with the present invention includes a flexible membrane 362 coupled to a more rigid annular ring 366 and having a substantially conical shape with a distal opening 364 for facilitating the passage of instruments therethrough. As shown, annular ring 366 preferably comprises a number of projections or tabs 368 extending in the distal direction around membrane 362. Tabs 368 serve to inhibit membrane 362 from collapsing in the proximal direction (termed "socking") so that membrane 362 remains patent during the surgical operation. In particular, tabs 368 hold membrane 362 substantially in the conical shape shown in FIGS. 17A and 17B when instruments are retracted proximally through opening 364.

Figure 18:
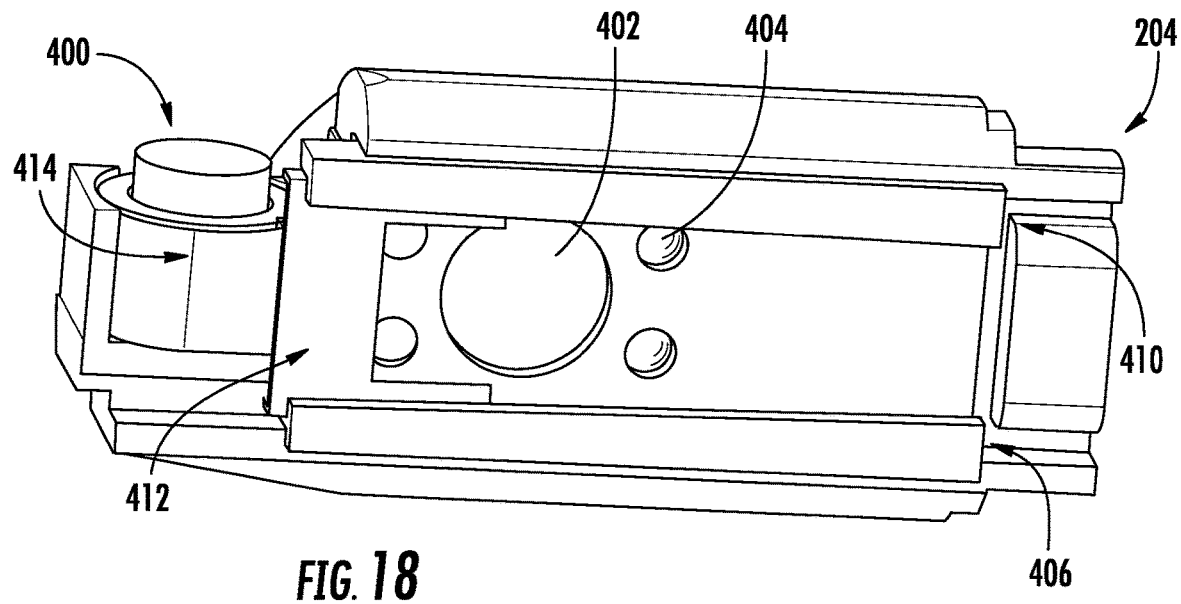
FIG. 18 illustrates a wiper mechanism for a camera lens of the cannula assembly according to the present invention.

Referring now to FIG. 18, cannula assembly 100 may further comprise a wiping assembly 400 for clearing fluids, tissue or other debris from the surface of a camera 402 within deployable housing 204. As shown, housing 204 includes an image transmission component, such as a camera 402 with a suitable lens, and illumination components, such as LEDs 404. A cover frame 406 attached to housing 204 contains openings for camera 402 and the LEDs 404 to illuminate and view the surgical site. Frame 406 includes channels 410 on either side of openings 408 and sized to receive a wiper shuttle 412. Wiper shuttle 412 is configured to translate through channels 410 and across openings 408 to clear debris from the surface of openings 408. Shuttle 412 is coupled to a suitable actuator, such as a constant force spring 414 positioned adjacent frame 406. Spring 414 is coupled to a suitable control mechanism in the proximal end of cannula assembly 100 to allow the operator to actuate spring 414 and cause shuttle 412 to translate through channels 410. In certain embodiments, the spring 414 is biased such that shuttle 412 is biased towards the spring 414 (i.e., in the position shown in FIG. 18). In use, the operator actuates spring 414 to force shuttle 412 through channels 410 and across openings 408. The biased spring 414 then automatically pulls wiper 412 back into its original position.

Figure 19:
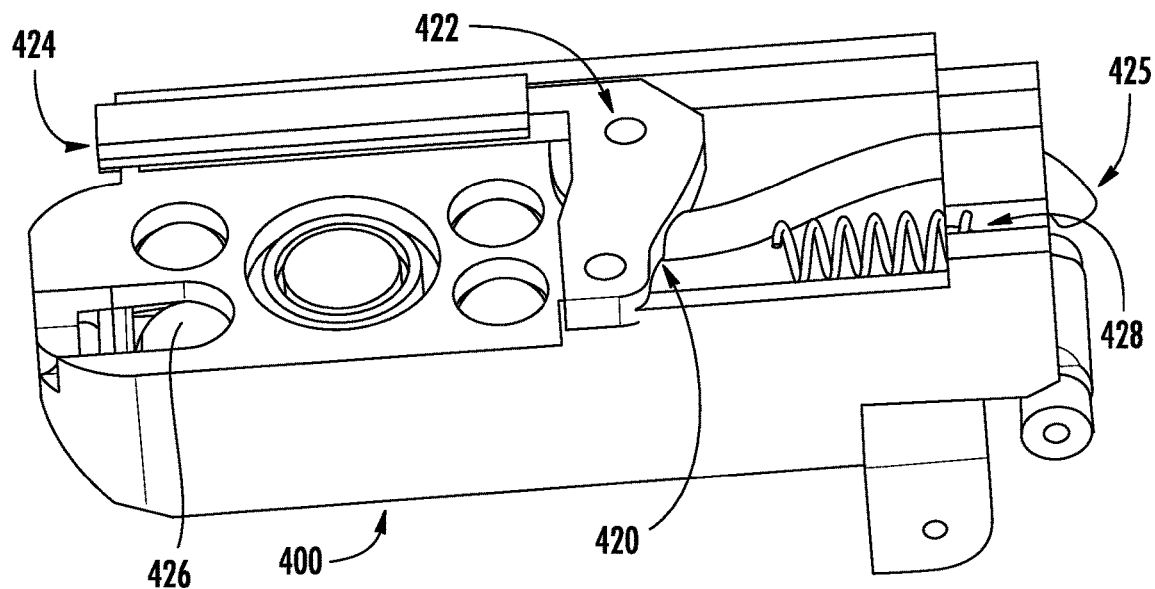
FIG. 19 illustrates another embodiment of a wiper assembly for a camera lens of the cannula assembly of the present disclosure.
Figure 20:
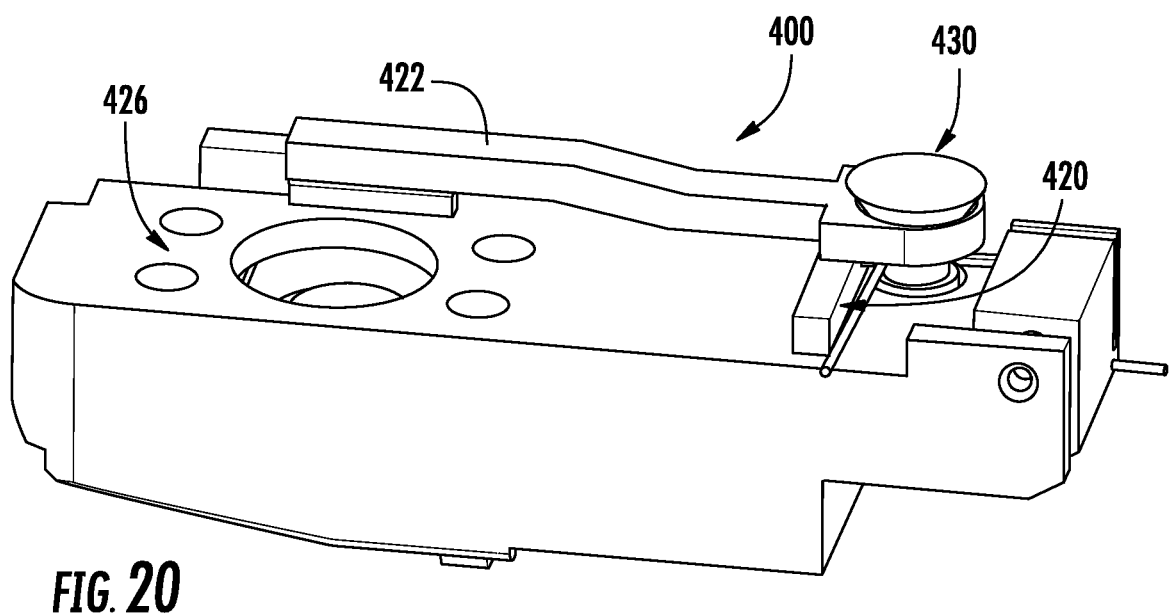
FIG. 20 illustrates another embodiment of a wiper assembly for a camera of the cannula assembly of the present disclosure.
Figure 21:
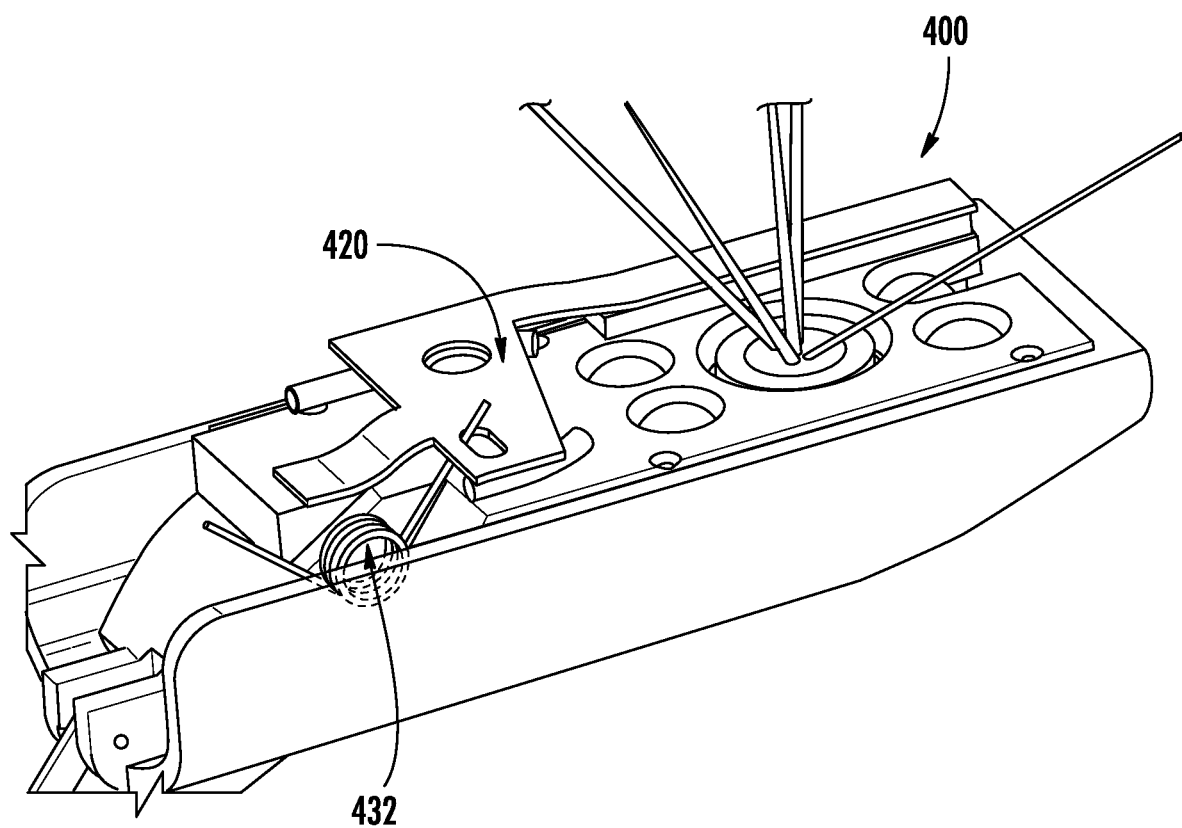
FIG. 21 illustrates yet another embodiment of a wiper assembly of the present disclosure.

FIGS. 19-21 illustrate alternative embodiments of the wiper assembly 400 of the present invention. As shown in FIG. 19, wiper assembly 400 includes a wiper shuttle 420 having a lateral arm 422 configured to translate through a channel 424 of housing 204. Wiper shuttle 420 is coupled to an actuator cable 425 configured to translate shuttle 420 in a longitudinal direction and cause wiper shuttle 420 to move across openings 426 for the camera and LEDs. Wiper assembly 400 may further comprise a spring 428 or other suitable biasing mechanism to bias shuttle 420 towards the position shown in FIG. 19 (i.e., where shuttle 420 does not block openings 426). FIG. 20 illustrates a similar design with rotatable actuator 430 and FIG. 21 illustrates a similar design with a torsion spring 432 for biasing shuttle 420. Torsion spring 430 may also be coupled to a suitable actuator mechanism (e.g., push rod, link, cable, etc.) to translate wiper shuttle 420 across openings 426.

Figure 22:
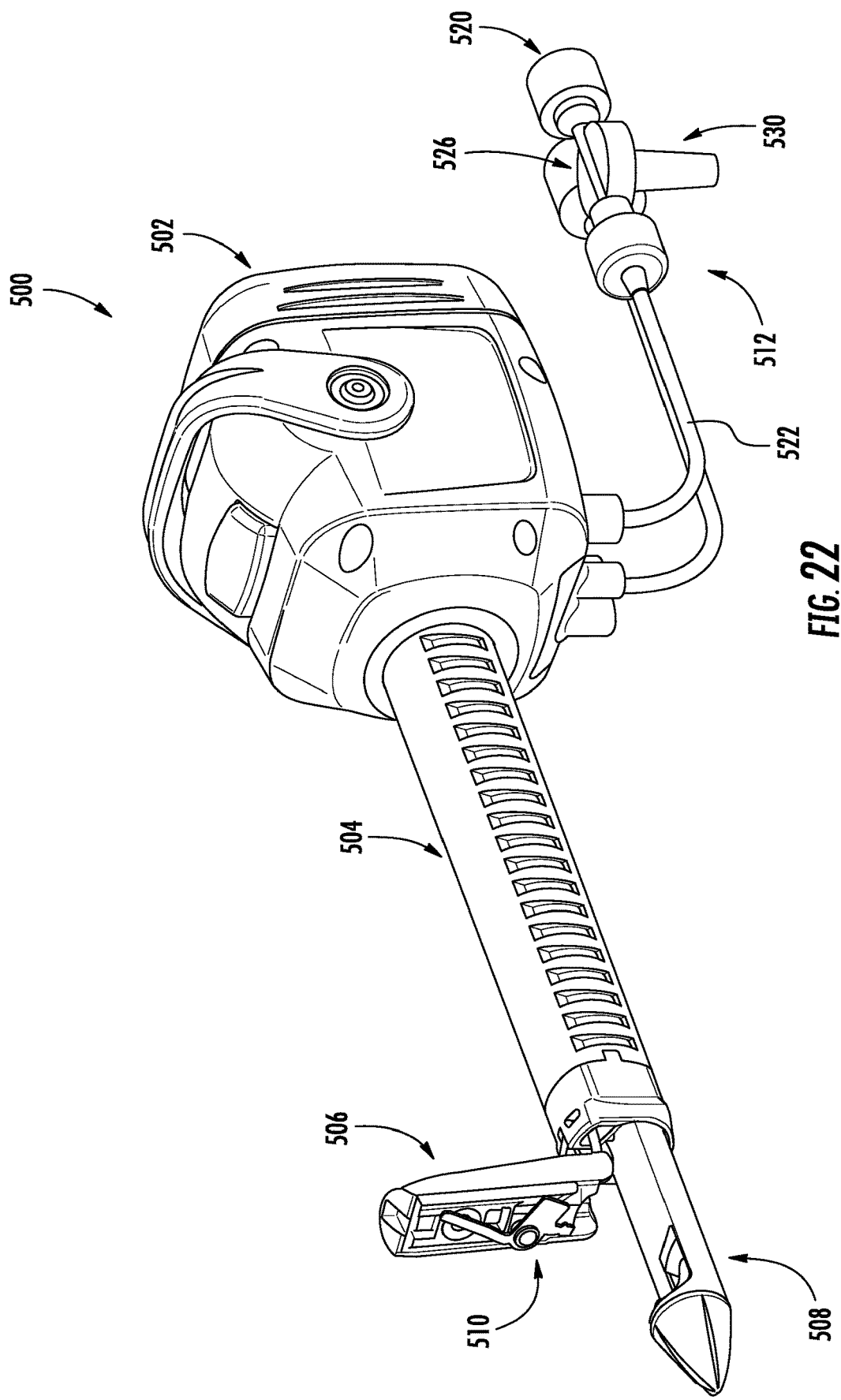
FIG. 22 illustrates a cannula assembly incorporating a wiper assembly and an irrigation assembly according to the present invention.
Figure 23B:
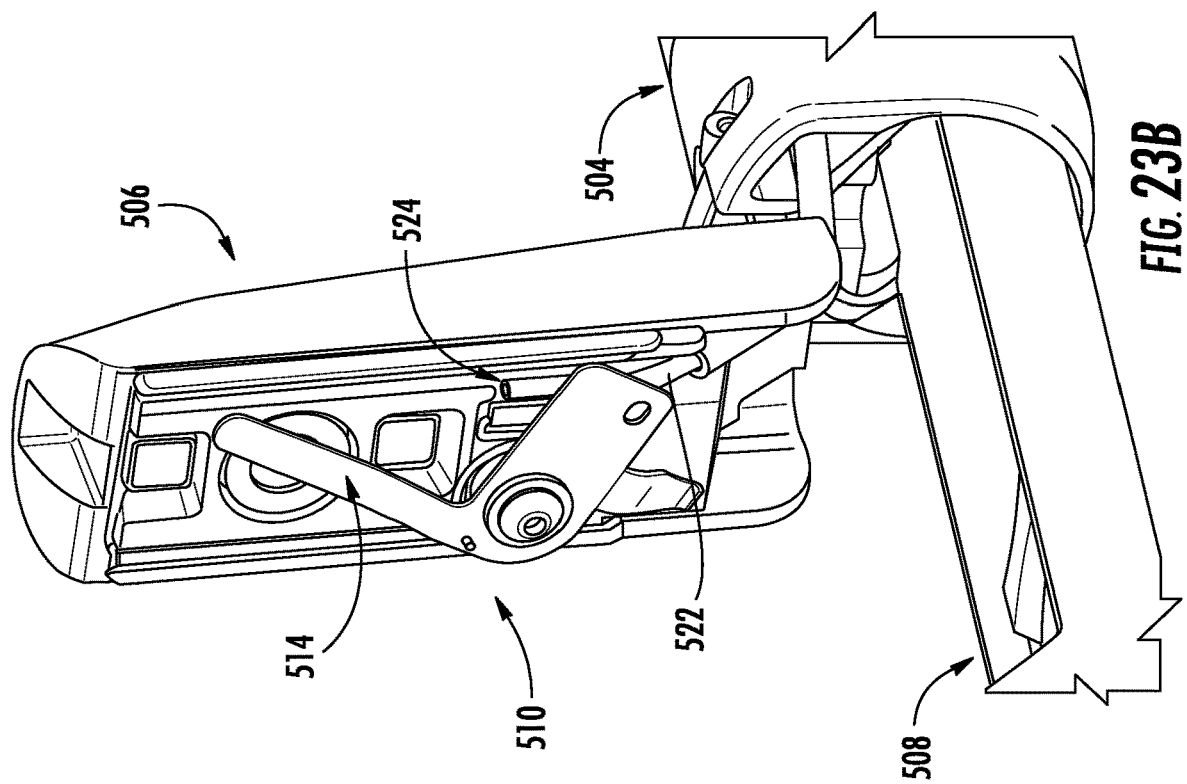
FIGS. 23A and 23B illustrate distal portions of the cannula assembly of FIG. 22.
Figure 23A:
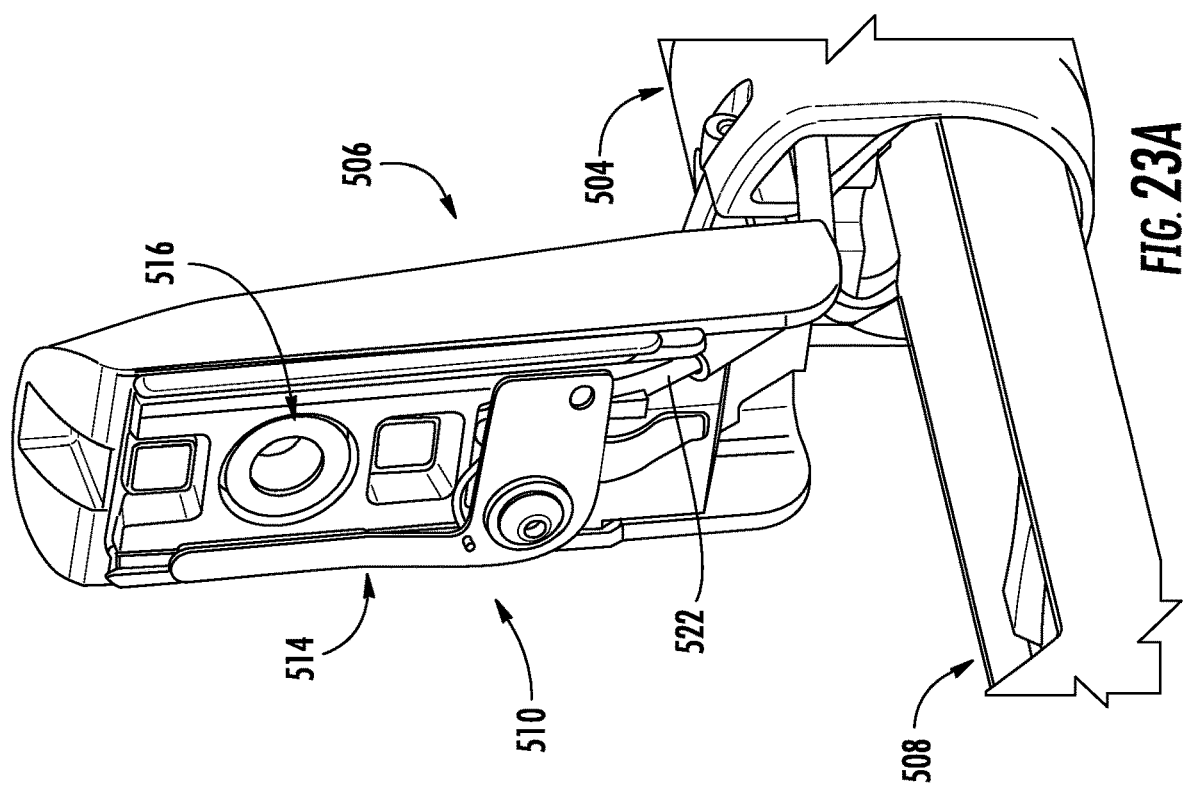

Referring now to FIGS. 22, 23A and 23B, a cannula assembly 500 according to the present invention includes a proximal handle 502, a tube 504 for passing through an incision or port in the patient, a deployable or movable camera housing 506 and a distal end portion 508 that is configured for longitudinal translation relative to tube 504 and housing 506 (similar to previous embodiments). Cannula assembly 500 further includes a wiper assembly 510 and an irrigation assembly 512. Wiper assembly 510 includes a wiper element 514 pivotally coupled to an inner surface of housing 506 and configured to move across the surface of a camera lens 516. Wiper element 514 is coupled to a suitable actuator mechanism that extends through tube 504 to proximal handle 502 to allow the operator to move wiper element 514 between the positions shown in FIGS. 23A and 23B.

Irrigation assembly 512 comprises a first proximal connector 520 for coupling assembly 512 to a suitable irrigation source, such as a syringe or the like, and an irrigation tube 522 that extends from connector 520 to housing 506. Irrigation tube 522 has an open distal end 524 positioned on an inner surface of housing 506 adjacent to the camera lens. Irrigation assembly 512 may further include a second proximal connector 530 adapted for coupling to a second fluid source, such as a saline or surfactant reservoir or the like, and a valve 546 positioned to open or close an internal lumen within irrigation tube 522.

Figure 24A:
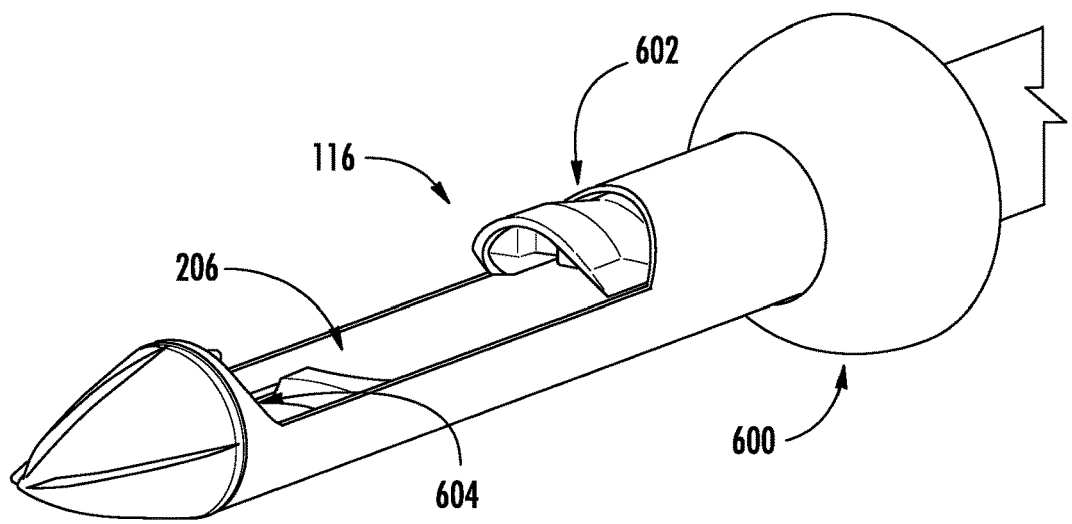
FIGS. 24A-24C illustrate a cover for the distal end portion of the cannula assembly according to certain embodiments of the invention.
Figure 24B:
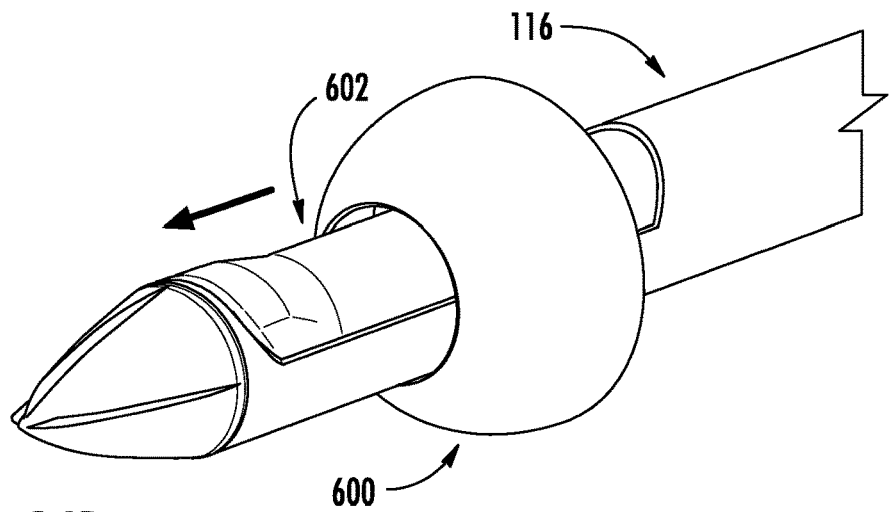
Figure 24C:
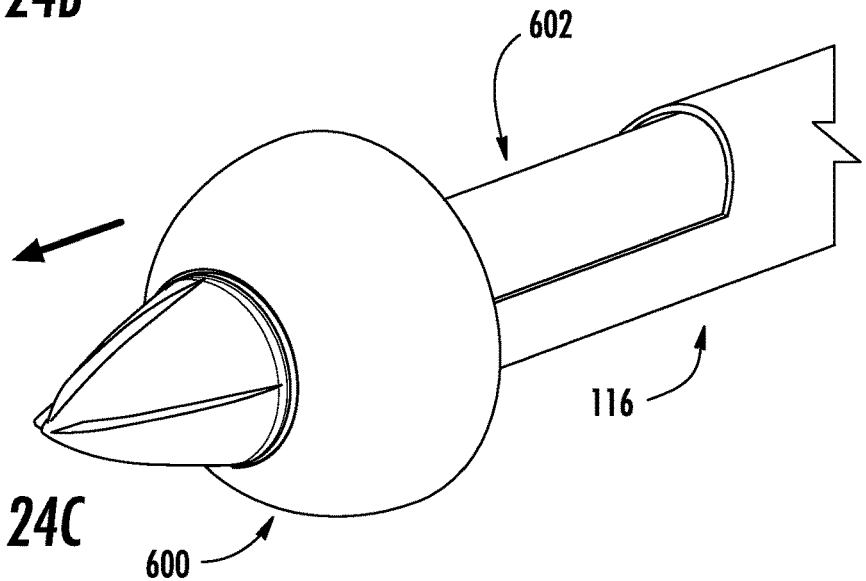

FIGS. 24A-24C illustrate another feature of the invention according to certain embodiments. As shown, distal end portion 116 is an obturator configured to advance distally and retract proximally relative to tube 110 (not shown). Distal end portion 116 includes a compartment 206 for housing deployable camera 204 (not shown) when distal end portion 116 is disposed within inner tube 110. A seal 600 is coupled to the inner surface of tube 110 within lumen 202. As discussed above, seal 600 provides a relatively tight fit between tube 110 and distal end portion 116 to contain gases and fluids and maintain a sterile enclosed surgical field within the patient. As distal end portion 116 is retracted proximally through lumen 202 of tube 110, seal 600 passes over distal end portion 116 and compartment 206 (as shown in FIGS. 24B and 24C).

According to the invention, distal end portion 116 further comprises a cover 602 movably coupled to distal end portion 116 and configured to advance distally and proximally over compartment 206. Cover 602 is coupled to a suitable actuating mechanism at the proximal end of cannula assembly 100 to move cover 602 proximally and distally relative to the remainder of distal end portion 116. Cover 602 serves to protect compartment 206 from seal 600 and to prevent the seal 600 from grabbing too tightly onto compartment 206 and/or catching on distal surface 604 of compartment 602 as it passes over the compartment 602.

In use, after the surgeon or operator has passed canula assembly 100 into the patient and moved housing/camera 206 into the open position (discussed above), cover 602 is advanced distally over compartment 602 with a suitable actuator (as shown in FIG. 24B). Distal end portion 116 may then be retracted proximally through lumen 202 of tube 110. As this occurs, seal 600 will slide over cover 602 without catching on an inner surface of compartment 602 or otherwise gripping down onto compartment 602.

In use, the user may pump saline, surfactant or other fluid(s) through irrigation tube 522 to its distal end and irrigate or spray the camera lens before deploying wiper assembly 510. This makes the wiper element more effective. The user may either connect a syringe or similar device to connector 520 to directly push the fluid through tube 522 via the syringe, or a fluid reservoir may be coupled to second connector 530 so that fluid is readily available during the procedure. The valve 526 can be used to close off irrigation tube 522 until the surgeon is ready to flush the surface of the camera pod.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A cannula assembly comprising:
a tube having a longitudinal axis, a proximal end portion and a distal end portion configured for insertion into a patient, the tube having an internal lumen extending from the proximal end portion to the distal end portion;
a housing rotatably coupled to the tube about an axis transverse to the longitudinal axis between a closed position and one or more open positions, wherein the housing has a distal end that is disposed on the tube proximal to the distal end portion and distal to the proximal end portion;
an electronic component comprising an image transmission device enclosed within the housing and being adapted to provide a longitudinal view when the housing is in the closed position and a transverse view relative to the longitudinal axis when the housing is in the open position; and
wherein the housing comprises a recess and the distal end portion of the tube comprises a projection extending substantially proximally along the longitudinal axis and configured to engage the housing within the recess when the housing is in the closed position.

2. The cannula assembly of claim 1 wherein the image transmission device at least partially blocks the internal lumen in the closed position.

3. The cannula assembly of claim 1 wherein the image transmission device is disposed laterally from the internal lumen relative to the longitudinal axis of the tube such that the internal lumen remains patent in the closed position.

4. The cannula assembly of claim 1 wherein the distal end portion of the tube is configured to create and pass through a percutaneous penetration in the patient.

5. The cannula assembly of claim 1 wherein the distal end portion is removably coupled to the tube and configured to translate in the longitudinal direction relative to the tube and the housing.

6. The cannula assembly of claim 5 wherein the distal end portion comprises:
a compartment for receiving housing when housing is in the closed position; and
a cover movably coupled to compartment and configured to advance distally and proximally along the longitudinal axis relative to compartment.

7. The cannula assembly of claim 1 wherein the distal end portion of the tube forms a pointed tip.

8. The cannula assembly of claim 1 wherein the distal end portion of the tube forms a blunt distal end.

9. The cannula assembly of claim 1 further comprising a removable trocar configured to pass through the lumen of the tube, the removable trocar being configured to create a percutaneous penetration in the patient.

10. The cannula assembly of claim 1 wherein the housing comprises a flexible hinge coupled to an outer surface of the tube and movable between the closed position, wherein the flexible hinge extends substantially along the longitudinal axis of the tube, and one or more of the open positions, wherein at least a portion of the flexible hinge bends away from the tube such that a distal portion of the housing is spaced from the tube and disposed at a transverse angle to the tube.

11. The cannula assembly of claim 1 further comprising:
a hinge pivotally coupling the housing to the tube; and
an actuator coupled to a proximal end of the housing and the hinge, the actuator being configured to cause the housing to rotate about the hinge relative to the tube.

12. The cannula assembly of claim 11 wherein the hinge comprises a cover plate sized to protect an exposed portion of the electronic component.

13. The cannula assembly of claim 1 further comprising a hinge pivotally coupling the housing to the tube, wherein the hinge is disposed on a lateral portion of the housing such that the image transmission device provides a lateral view in the open position.

14. The cannula assembly of claim 1 further comprising a hinge pivotally coupling the housing to the tube, wherein the hinge is disposed on a distal portion of the housing such that the image transmission device provides a proximal view in the open position.

15. The cannula assembly of claim 1 further comprising one or more reflective surfaces positioned within the tube so as to reflect light from the image transmission device through the distal end portion of the tube when the housing is in the closed position and a substantially opaque wall positioned within the tube to inhibit backscatter of light from the image transmission device when the housing is in the closed position.

16. The cannula assembly of claim 15 wherein the mirror and the substantially opaque wall remain fixed to the tube when the housing is moved towards the open position.

17. The cannula assembly of claim 1 further comprising a seal within the lumen configured to allow passage of instruments through the seal and to inhibit passage of gases and liquids through the seal.

18. The cannula assembly of claim 1 wherein the image transmission device includes a camera with a lens, the cannula assembly further comprising a wiper assembly housed within the tube, the wiper assembly comprising an actuator and a wiper element, the actuator being configured to move the wiper element relative to the lens to clean a surface of the lens.

19. The cannula assembly of claim 18 further comprising a flexible tube having a proximal end configured for coupling to a source of fluid and a distal end within the housing adjacent to or near the wiper element.

20. A cannula assembly comprising:
a tube having a longitudinal axis, a proximal end portion and a distal end portion, the distal end portion being configured for insertion into a body cavity of a patient, the tube having an internal lumen extending from the proximal end portion to the distal end portion;
a housing rotatably coupled to the tube at least partially about the longitudinal axis between one or more open positions and a closed position, wherein the housing is disposed at least partially lateral of the tube in the open position;
an electronic component comprising an image transmission device housed within the housing and disposed laterally from the internal lumen relative to the longitudinal axis of the tube, the image transmission device being adapted to provide a longitudinal view when the deployable portion is in the closed position and a lateral view relative to the longitudinal axis when the deployable portion is in the one or more open positions; and
wherein the housing comprises a recess and the distal end portion of the tube comprises a projection extending substantially proximally along the longitudinal axis and configured to engage the housing within the recess when the housing is in the closed position.

21. The cannula assembly of claim 20 wherein further comprising a hinge pivotally coupling the housing to the tube, wherein the hinge is disposed on a distal portion of the housing.

22. The cannula assembly of claim 20 wherein the housing is rotatably coupled to the tube about two or more axes transverse to the longitudinal axis.

23. The cannula assembly of claim 20 wherein the housing is disposed proximal to the distal end portion of the tube and distal to the proximal end portion of the tube.

24. A cannula assembly comprising:
a tube having a longitudinal axis, a proximal end and a distal end, the distal end being configured for insertion into a body cavity of a patient, the tube having an internal lumen extending from the proximal end to the distal end;
a housing rotatably coupled to the tube between one or more open positions and a closed position and having an interior, wherein the housing has a distal end disposed proximal to the distal end portion of the tube and distal to the proximal end portion of the tube;
an electronic component comprising an image transmission device contained within an interior of the housing and being adapted to provide a longitudinal view when the housing is in the closed position and a transverse view relative to the longitudinal axis when the housing is in the one or more open positions; and
wherein the housing comprises a recess and the distal end of the tube comprises a projection extending substantially proximally along the longitudinal axis and configured to engage the housing within the recess when the housing is in the closed position.

25. The cannula assembly of claim 24 wherein the housing comprises a wall around the interior and the projection comprises a lip extending from the wall into the interior of the housing.

26. The cannula assembly of claim 24 wherein the projection extends from the distal end portion of the tube into the interior of the housing.

* * * * *